US009198800B2

(12) United States Patent
Killion et al.

(10) Patent No.: US 9,198,800 B2
(45) Date of Patent: Dec. 1, 2015

(54) ELECTRONIC EARPLUG FOR PROVIDING COMMUNICATION AND PROTECTION

(71) Applicant: Etymotic Research, Inc., Elk Grove Village, IL (US)

(72) Inventors: Mead C. Killion, Elk Grove Village, IL (US); James Collins, Elk Grove Village, IL (US); Timothy Scott Monroe, Schaumburg, IL (US); Russ Thoma, Gurnee, IL (US); Viorel Drambarean, Lincolnwood, IL (US); Andrew Haapapuro, Arlington Heights, IL (US); Jerrold Zdenek, Deer Park, IL (US)

(73) Assignee: ETYMOTIC RESEARCH, INC., Elk Grove Village, IL (US)

( * ) Notice: Subject to any disclaimer, the term of this patent is extended or adjusted under 35 U.S.C. 154(b) by 138 days.

(21) Appl. No.: 14/156,023

(22) Filed: Jan. 15, 2014

(65) Prior Publication Data
US 2014/0198926 A1 Jul. 17, 2014

Related U.S. Application Data

(60) Provisional application No. 61/752,773, filed on Jan. 15, 2013.

(51) Int. Cl.
*A61F 11/06* (2006.01)
*H04R 1/10* (2006.01)
(Continued)

(52) U.S. Cl.
CPC .............. *A61F 11/08* (2013.01); *H04R 1/1041* (2013.01); *H04R 1/086* (2013.01); *H04R 3/005* (2013.01); *H04R 2201/003* (2013.01); *H04R 2400/01* (2013.01)

(58) Field of Classification Search
CPC .... H04R 1/1016; H04R 1/1083; H04R 5/033; H04R 17/02; H04R 1/08; H04R 2201/107; H04R 2460/01; H04R 3/005; G10K 2210/1081; G10K 2210/108; H04M 1/0258
USPC ............... 381/328, 72, 74, 312, 375; 181/135
See application file for complete search history.

(56) References Cited

U.S. PATENT DOCUMENTS

| 1,355,276 A | 10/1920 | Shultz |
| 2,246,737 A | 6/1941 | Knudsen |

(Continued)

FOREIGN PATENT DOCUMENTS

| WO | 8803740 | 5/1988 |
| WO | 03032681 A1 | 4/2003 |

*Primary Examiner* — Paul S Kim
*Assistant Examiner* — Norman Yu
(74) *Attorney, Agent, or Firm* — McAndrews, Held & Malloy, Ltd.

(57) ABSTRACT

Systems and methods for providing communication and protection by an electronic earplug are provided. A communication and protection system includes an electronic earplug operable in a transmit mode and a receive mode. The electronic earplug includes an external microphone, an ear canal microphone, processing circuitry, and a receiver. In the receive mode, the external microphone is configured to transduce sound pressure levels received from exterior to an ear canal to electrical signals; the processing circuitry is configured to process the electrical signals from the external microphone to provide processed electrical signals; and, the receiver is configured to convert the processed electrical signal to sound. In the transmit mode, the ear canal microphone is configured to transduce sound pressure levels received from in the ear canal to electrical signals provided to a communication device; and, one or more of the external microphone, the processing circuitry, and the receiver is disabled.

31 Claims, 16 Drawing Sheets

(51) Int. Cl.
*A61F 11/08* (2006.01)
*H04R 25/00* (2006.01)
*H04R 1/08* (2006.01)
*H04R 3/00* (2006.01)

(56) References Cited

U.S. PATENT DOCUMENTS

| | | | |
|---|---|---|---|
| 2,427,664 A | 9/1947 | Dunbar et al. |
| 2,430,229 A | 11/1947 | Kelsey |
| 2,487,038 A | 11/1949 | Baum |
| 2,824,558 A | 2/1958 | Michael et al. |
| 2,888,921 A | 6/1959 | Nielson et al. |
| 3,209,082 A | 9/1965 | McCarrell et al. |
| 3,890,474 A | 6/1975 | Glicksberg |
| 4,006,796 A | 2/1977 | Coehorst |
| RE29,487 E | 12/1977 | Gardner, Jr. |
| 4,150,262 A | 4/1979 | Ono |
| 4,442,917 A | 4/1984 | Johnson |
| 4,459,247 A | 7/1984 | Rothemund |
| 4,975,967 A | 12/1990 | Rasmussen |
| 5,298,692 A | 3/1994 | Ikeda et al. |
| 5,396,563 A | 3/1995 | Yoshimi |
| 5,832,094 A | 11/1998 | Le Her |
| 6,175,633 B1 | 1/2001 | Morrill et al. |
| 6,339,648 B1 | 1/2002 | McIntosh et al. |
| 6,366,863 B1 | 4/2002 | Bye et al. |
| 6,415,034 B1 | 7/2002 | Hietanen |
| 6,493,453 B1 | 12/2002 | Glendon |
| 6,647,345 B2 | 11/2003 | Bye et al. |
| 6,735,319 B1 | 5/2004 | Vonlanthen |
| 6,741,718 B1 | 5/2004 | Brumitt et al. |
| 6,851,048 B2 | 2/2005 | Armitage |
| 6,888,948 B2 | 5/2005 | Hagen et al. |
| 6,895,345 B2 | 5/2005 | Bye et al. |
| 7,340,231 B2 | 3/2008 | Behrens et al. |
| 7,352,871 B1 | 4/2008 | Mozo |
| 7,370,655 B2 | 5/2008 | Taylor |
| 7,451,256 B2 | 11/2008 | Hagen et al. |
| 7,757,400 B2 | 7/2010 | Widmer et al. |
| 7,787,647 B2 | 8/2010 | Hagen et al. |
| 7,793,663 B2 | 9/2010 | Taylor |
| 7,891,360 B2 | 2/2011 | Buck et al. |
| 7,929,723 B2 | 4/2011 | Hagen et al. |
| 8,300,862 B2 | 10/2012 | Newton et al. |
| 9,058,801 B2 * | 6/2015 | Po et al. ............... 1/1 |
| 2009/0029743 A9 * | 1/2009 | Lair et al. ........... 455/569.1 |
| 2012/0097475 A1 | 4/2012 | Schumaier |

* cited by examiner

ELECTRONIC EARPLUG FOR PROVIDING COMMUNICATION AND PROTECTION

CROSS-REFERENCE TO RELATED APPLICATIONS/INCORPORATION BY REFERENCE

The present application claims priority under 35 U.S.C. §119(e) to provisional application Ser. No. 61/752,773, filed on Jan. 15, 2013. The above referenced provisional application is hereby incorporated herein by reference in its entirety.

U.S. patent application Ser. No. 12/914,314, by Killion et al., published May 5, 2011 as U.S. Publication No. 2011/0103605, is incorporated by reference herein in its entirety.

U.S. patent application Ser. No. 13/150,798, by Killion et al., published Sep. 22, 2011 as U.S. Publication No. 2011/0228937, is incorporated by reference herein in its entirety.

U.S. Provisional Application Ser. No. 61/256,807 filed on Oct. 30, 2009, entitled Electronic Earplug, is incorporated by reference herein in its entirety.

U.S. Provisional Application Ser. No. 61/298,755 filed on Jan. 27, 2010, entitled Electronic Earplug, is incorporated by reference herein in its entirety.

U.S. Provisional Application Ser. No. 61/299,232 filed on Jan. 28, 2010, entitled Two-Way Communication Device With Multiple Microphones, is incorporated by reference herein in its entirety.

U.S. Provisional Application Ser. No. 61/313,201 filed on Mar. 12, 2010 entitled, Telecoil Option For Electronic Blast Plug And Quiet Sound Amplifier Products, is incorporated by reference herein in its entirety.

U.S. Provisional Application Ser. No. 61/386,344 filed on Sep. 24, 2010, entitled Wireless Two-Way Communication Device Using A Single Coil, is incorporated by reference herein in its entirety.

U.S. Provisional Application Ser. No. 61/439,524 filed on Feb. 4, 2011, entitled Bipolar HI-LO Gain Switch with Click and Tone for Electronic Blast Plug Integrated Circuit, is incorporated by reference herein in its entirety.

U.S. Pat. No. 4,592,087 issued to Killion on May 27, 1986, is incorporated by reference herein in its entirety.

U.S. Pat. No. 4,677,679 issued to Killion on Jun. 30, 1987, is incorporated by reference herein in its entirety.

U.S. Pat. No. 4,689,819 issued to Killion on Aug. 25, 1987, is incorporated by reference herein in its entirety.

U.S. Pat. No. 5,131,046 issued to Killion et al. on Jul. 14, 1992, is incorporated by reference herein in its entirety.

U.S. Pat. No. 5,623,550 issued to Killion et al. on Apr. 22, 1997, is incorporated by reference herein in its entirety.

U.S. Pat. No. 5,812,679 issued to Killion et al. on Sep. 22, 1998, is incorporated by reference herein in its entirety.

U.S. Pat. No. 6,047,075 issued to Killion et al. on Apr. 4, 2000, is incorporated by reference herein in its entirety.

U.S. Pat. No. 6,320,969 issued to Killion et al. on Nov. 20, 2001, is incorporated by reference herein in its entirety.

U.S. Pat. No. 6,466,678 issued to Killion et al. on Oct. 15, 2002, is incorporated by reference herein in its entirety.

U.S. Pat. No. RE 38,351 issued to Iseberg et al. on Dec. 16, 2003, is incorporated by reference herein in its entirety.

U.S. Pat. No. 6,694,034 issued to Julstrom et al. on Feb. 17, 2004, is incorporated by reference herein in its entirety.

U.S. Pat. No. 6,704,424 issued to Killion et al. on Mar. 9, 2004, is incorporated by reference herein in its entirety.

U.S. Pat. No. 7,099,486 issued to Julstrom et al. on Aug. 29, 2006, is incorporated by reference herein in its entirety.

U.S. Pat. No. 7,206,426 issued to Julstrom et al. on Apr. 17, 2007, is incorporated by reference herein in its entirety.

U.S. Pat. No. 7,522,740 issued to Julstrom et al. on Apr. 21, 2009, is incorporated by reference herein in its entirety.

U.S. Pat. No. 8,160,284 issued to Johnson et al. on Apr. 17, 2012, is incorporated by reference herein in its entirety.

FEDERALLY SPONSORED RESEARCH OR DEVELOPMENT

[Not Applicable]

MICROFICHE/COPYRIGHT REFERENCE

[Not Applicable]

BACKGROUND OF THE INVENTION

It is highly documented that military personnel exposed to blasts from firearms, explosions and other high level peak noises are at high risk for hearing loss. It has been estimated that 68% of deployed soldiers return with ear damage, and 100% do not protect both ears during combat. (Saunders and Griest, "Hearing loss in veterans and the need for hearing loss prevention programs" NHCA Meeting, Portland Oreg., Feb. 23, 2008). In 2007, it was estimated that the cost of hearing aids for soldiers was $141.3 million and the cost for clinical services (not including hearing aids) was $147.1 million. (Saunders and Griest, "Hearing loss in veterans and the need for hearing loss prevention programs" NHCA Meeting, Portland Oreg., Feb. 23, 2008).

Sound pressure levels (SPLs) over 160 dB that occur over periods as short as even a few milliseconds are sufficient to cause damage to the unprotected ear. Exposure to the peak noises caused by gunfire or other explosions adds hearing loss to the long list of risks and dangers encountered by soldiers on the battle field. One means to prevent hearing loss is to wear a noise attenuating device such as ear plugs or earmuffs. U.S. Pat. No. 5,203,352 issued to Gardner presents high-attenuation foam earplugs which may provide up to 40 dB of attenuation when properly inserted. Accordingly, the Gardner earplugs will reduce hazardous external peak SPLs of 160 to 190 dB to safer levels of 120 to 150 dB, respectively, within the ear canal of the wearer.

The Gardner and other similar earplugs will attenuate up to 40 dB of noise, but the attenuation level is independent of the level external sound. In other words, all external noises will be attenuated the same amount whether the sounds are extremely loud or very soft. Thus, softer sounds that would otherwise be audible without the use of earplugs may become inaudible or become so soft that they go unnoticed. For many work environments the perception of soft sounds is vital to the task at hand or the safety of the workers. For example, a soldier wearing earplugs as described attenuating a constant 40 dB of noise may fail to hear an enemy quietly approaching or fail to perceive communications from fellow soldiers. Likewise, a construction worker wearing such earplugs may receive adequate protection from high level construction sounds, but fail to hear a distant coworker's emergency call for help.

Many earplugs, like those described by Gardner, for example, may distort the reception of normal sound. The earplugs attenuate higher frequency sounds at a higher level than lower frequency sounds making it difficult for the wearer to hear or understand speech and other important sounds. High-audibility earplugs such as those described by U.S. Pat. No. 4,807,612 issued to Carlson and used in the ER-9®, the ER-15®, and the ER-25® series Musicians Earplugs® produced by Etymotic Research, Inc., and having nominal 9 dB, 15 dB, and 25 dB attenuation respectively, and as described in U.S. Pat. No. 5,113,967 issued to Killion et al., and used in products such as the ER-20® series HiFi earplugs produced by Etymotic Research, Inc.®, all produce relatively uniform attenuation across audible frequency ranges and a low enough attenuation such that speech and music remain highly audible to the wearer. While the high audibility of these earplugs allows the wearer to hear softer noises, they may not provide adequate protection for extremely high level sounds. Moreover, even the lowest-attenuation ER-9 earplug may produce unacceptable attenuation for a soldier who needs to have the best chance of hearing a quietly approaching enemy. Moreover 9 dB attenuation is insufficient to protect the soldier's ears from many high-energy noise levels that occur during battle.

An earplug with sound level dependent attenuation is described in U.S. Pat. No. 4,924,502 issued to Allen, et al. and U.S. Pat. No. 5,936,208 issued to Hamery and is embodied in a product sold by AEARO Technologies under the trade name Combat Arms Earplug. The Combat Arms Earplug introduces less noise attenuation for external SPLs below 110 dB than for external SPLs above 110 dB, but does not provide a constant attenuation across all frequencies. For example, where the external SPL is below 110 dB the Combat Arms Earplug provides around 5 dB of attenuation at very low frequencies and up to 23 dB attenuation at higher frequencies. Where the external SPL is above 110 dB, the attenuation provided increases by approximately 0.3 dB for each 1 dB increase of external sound until a maximum level of attenuation is achieved. For example a 9 dB change for 110-150 input gives 9/40=0.23 dB/dB. For the 150-190 range, the attenuation may increase another 12 dB in that 40 dB range, or 0.3 dB/dB. The Combat Arms Earplug provides a passageway that allows partially unobstructed travel of sound from the exterior into the ear canal with a relatively low level of attenuation at low sound pressure levels. A sharp obstruction located within the passageway of the Combat Arms Earplug causes the flow of sound within the earplug to become turbulent above 110 dB. This introduction of turbulent flow impedes the flow of the sound into the ear, thereby establishing greater attenuation. While the aforementioned earplugs may provide non-linear pattern attenuation, they do not provide enough audibility for low-level sounds: The 15-23 dB attenuation they provide between 1 kHz and 3 kHz (Berger and Hamery "Empirical evaluation using impulse noise of the level-dependency of various passive earplug designs;" Presentation at Acoustics Paris 2008 J. Acoust Soc. Am. 123 (5, Pt. 2), p. 3528) is apparently too much to provide good situation awareness for the soldier. As a result, "Many troops say they don't use hearing protection on missions because they feel it affects their situational awareness, ability to do their jobs and complete their missions" according to Dr. Joseph Brennan in an Army Times staff report "Troops reject ear protection in Afghanistan" Posted: Wednesday Aug. 26, 2009 5:29:32 EDT. Other estimates are that 68% of deployed soldiers return with ear damage, and the majority refuse to wear earplugs, costing some $288 million each year in auditory rehabilitation (Saunders and Griest, "Hearing loss in veterans and the need for hearing loss prevention programs" NHCA Meeting, Portland Oreg., Feb. 23, 2008).

It seems clear from the refusal of soldiers to wear existing hearing protection that no existing devices provide the combination of situational awareness (especially for quiet sounds) and blast protection that is needed.

Electronic hearing protection would appear to be a better solution, and indeed has also been known for many years. A popular form is the "Walker Game Ear" device. This and similar forms typically provide some gain for quiet sounds under the assumption that the typical hunter purchaser already has some hearing loss so that a combination hearing aid and hearing protection would be beneficial. They all have in common that they use a tiny hearing aid receiver whose maximum output of 110-125 dB is further limited by a limited power available from the output amplifier in the hearing aid. Thus the peak pressure from a firearm of typically or 170 dB is reduced to a snap of less than 130 dB, which is safe for the 1 or 2 milliseconds of the pulse duration. According to Berger, firearms, howitzers and roadside explosions typically fall in the range of 150 to 180 dB SPL. This electronic approach is well known to the applicant, since the "K-AMP" hearing aid (which was designed by Etymotic Research, described in U.S. Pat. No. 5,131,046, and manufactured by nearly every hearing aid company in the 1990s) was used for hearing protection by many including one of its own employees while hunting. The K-AMP Hearing Aid had the advantage that it provided normal localization for the hunter and near-normal "situational awareness," but a drawback was that it had to be built into a custom earmold shell which typically required 2-3 visits to a licensed hearing aid dispenser.

The problem with all present devices is that they do not provide a low-cost, ready-to-wear, high-fidelity device with a 16 kHz bandwidth, suitable for the normal-hearing soldier. The lack of understanding that this is even possible is indicated perhaps by the fact that in many pages of Army "SBIR" requests for proposals perused by the applicant, none of them describe the type of device that the applicant has developed, or apparently even imagined that it was possible.

Additionally, many existing devices do not provide the capability to couple with radios or other communication devices. Existing devices with communication capability typically are in the form of an earmuff communication headset with a boom microphone, such as the Peltor ComTac II tactical headset. However, earmuff communication headsets are bulky and may not fit comfortably under a soldier's helmet, for example.

Further limitations and disadvantages of conventional and traditional approaches will become apparent to one of skill in the art, through comparison of such systems with some aspects of the present invention as set forth in the remainder of the present application.

SUMMARY OF THE INVENTION

Certain embodiments of the present technology provide electronic earplugs for providing communication and protection, substantially as shown in and/or described in connection with at least one of the figures.

These and other advantages, aspects and novel features of the present invention, as well as details of an illustrated embodiment thereof, will be more fully understood from the following description and drawings.

BRIEF DESCRIPTION OF THE DRAWING(S)

DETAILED DESCRIPTION OF PREFERRED EMBODIMENT(S)

Figure 1:
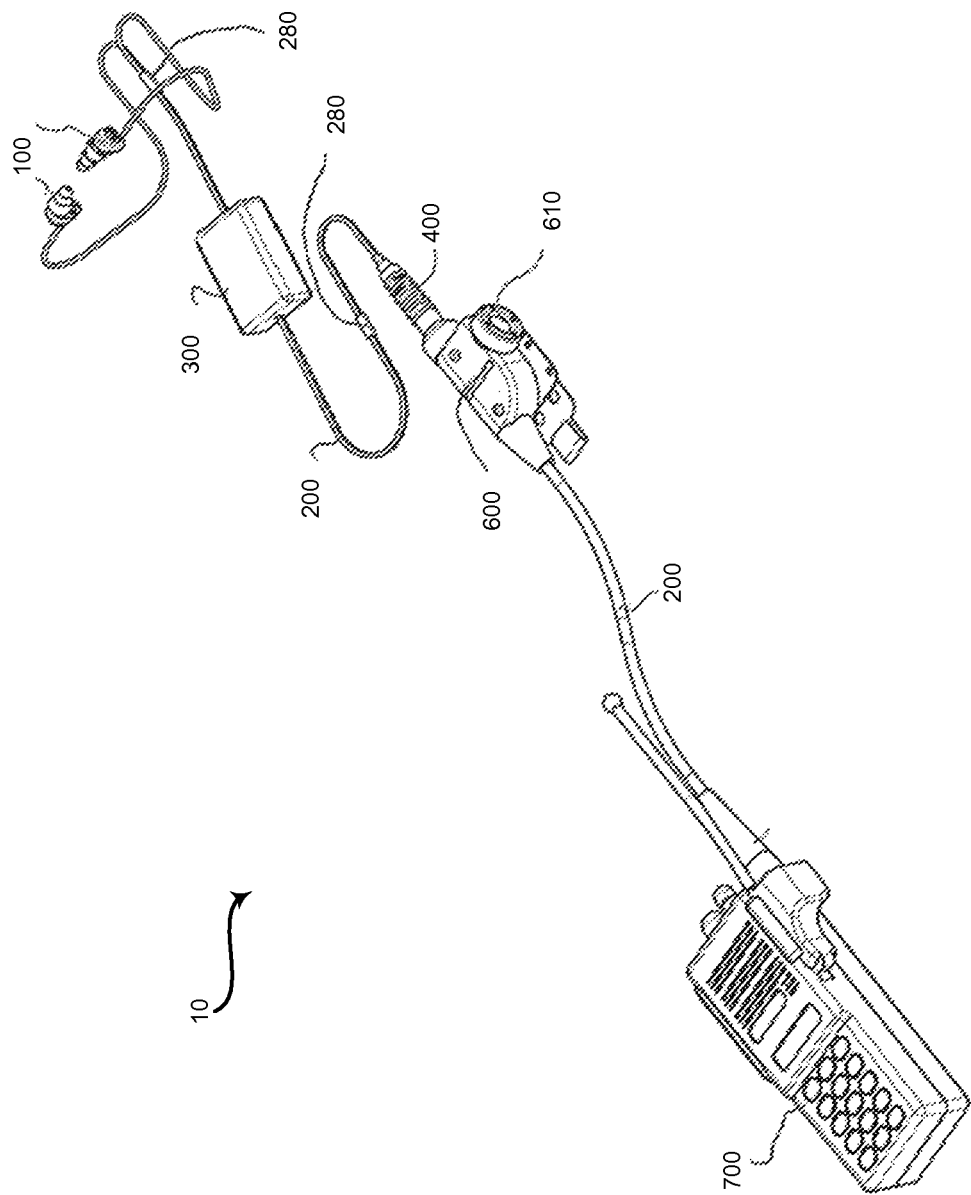
FIG. 1 depicts an exemplary communication and protection system comprising a communication radio, a push to talk assembly, a battery module, cables, and electronic earplugs used in accordance with embodiments of the present technology.

Embodiments of the present technology provide electronic earplugs for providing communication and protection. More specifically, certain embodiments provide a first electronic earplug and a second electronic earplug. The first electronic earplug can provide processed sound from the exterior microphone to the ear canal when in receive mode, and one or more of a receiver, processing circuitry, and an exterior microphone of the first electronic earplug may be disabled when in transmit mode such that sound from an ear canal microphone can be provided to the communication radio for transmission. The second electronic earplug may provide processed sound from an exterior microphone to the ear canal when in a transmit mode, and processed sound from the exterior microphone mixed with sound received from a communication radio when in receive mode.

The foregoing summary, as well as the following detailed description of certain embodiments will be better understood when read in conjunction with the appended drawings. It should be understood that the various embodiments are not limited to the arrangements and instrumentality shown in the drawings. It should also be understood that the embodiments may be combined, or that other embodiments may be utilized and that structural, logical and electrical changes may be made without departing from the scope of the various embodiments of the present invention. The following detailed description is, therefore, not to be taken in a limiting sense, and the scope of the present invention is defined by the appended claims and their equivalents.

FIG. 1 depicts an exemplary communication and protection system 10 comprising a communication radio 700, a push to talk assembly 600, a battery module 300, cables 200, and electronic earplugs 100 used in accordance with embodiments of the present technology. The communication radio 700 may be a handheld transceiver, mobile phone, or any suitable communication device.

The push to talk assembly 600 couples the communication radio 700 with the electronic earplugs 100. The push to talk assembly 600 comprises a switch 610, such as a momentary switch or any suitable switching mechanism, for switching between a transmit mode and a reception mode. For example, when a switch 610 of the push to talk assembly 600 is actuated, the communication system 10 may be operable to transmit communications, and when the switch 610 is not actuated, the system 10 can be operable to receive communications. The push to talk assembly 600 may comprise a cable 200 comprising a plug 400 for coupling with the communication radio. The push to talk assembly 600 can comprise a jack for receiving a plug 400 of the battery module 300 and/or the electronic earplugs 100, for example.

Figure 6:
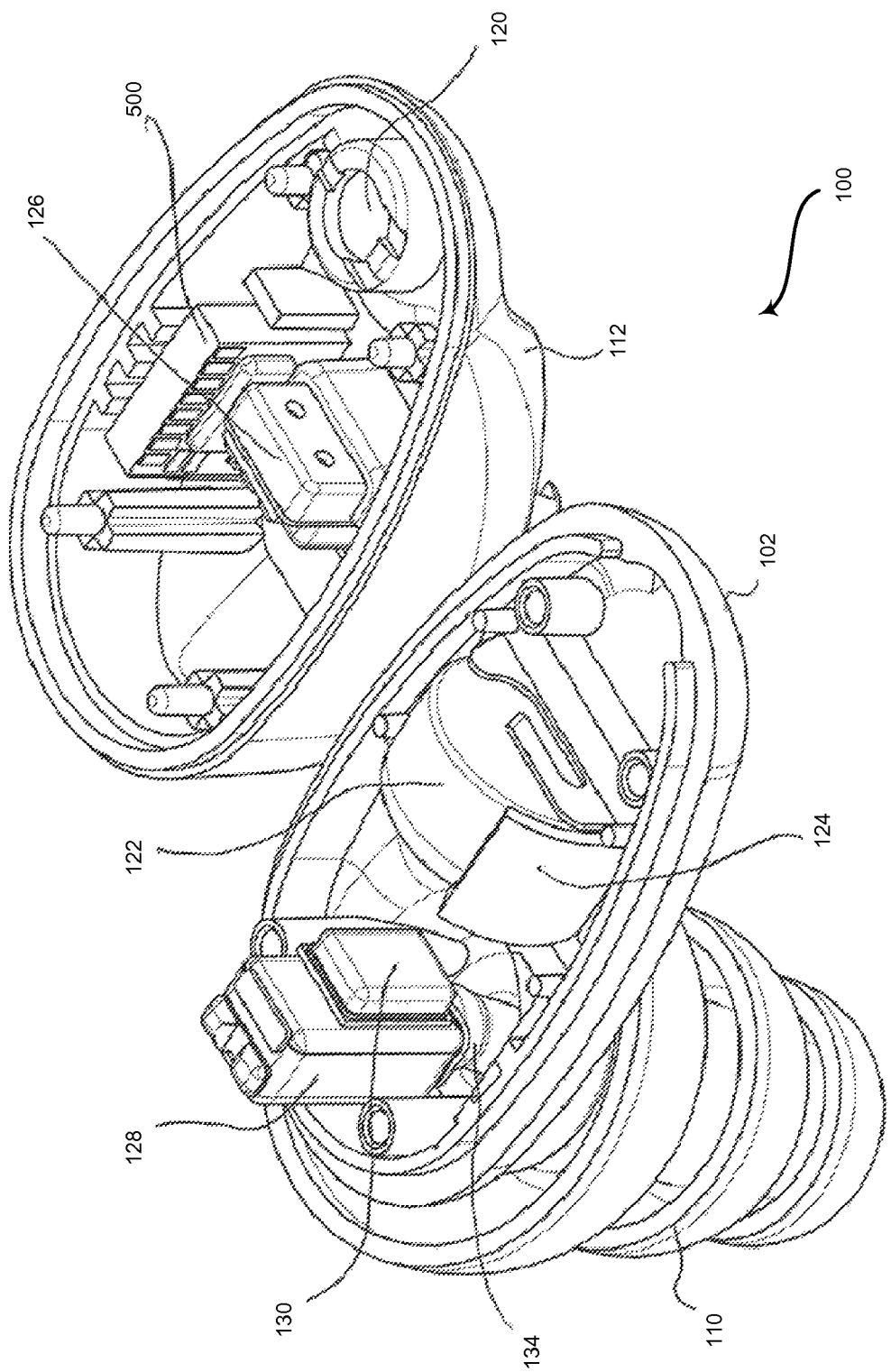
FIG. 6 depicts an exemplary electronic earplug with a canal microphone used in accordance with embodiments of the present technology.
Figure 7:
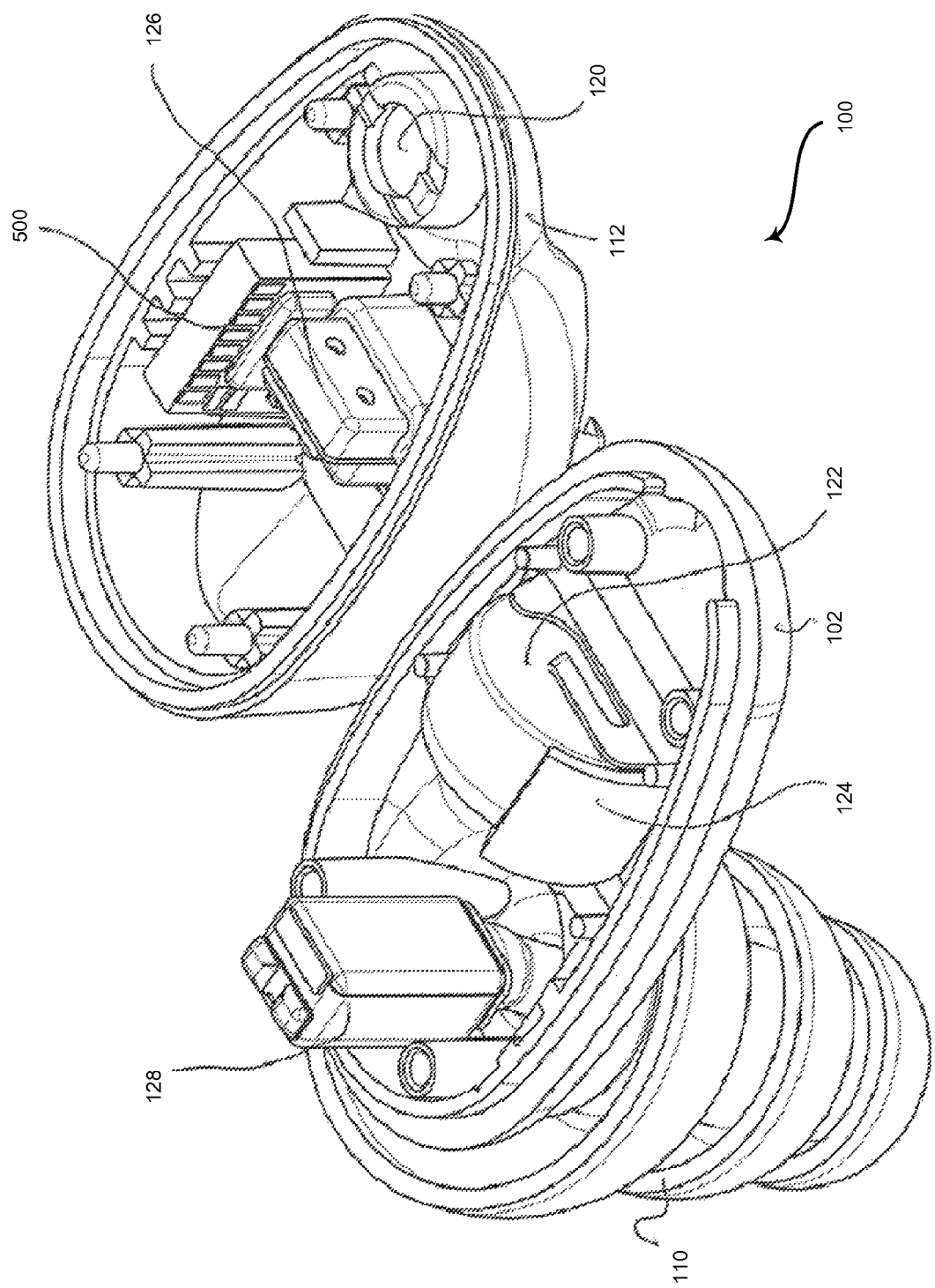
FIG. 7 depicts an exemplary electronic earplug without a canal microphone used in accordance with embodiments of the present technology.
Figure 9:
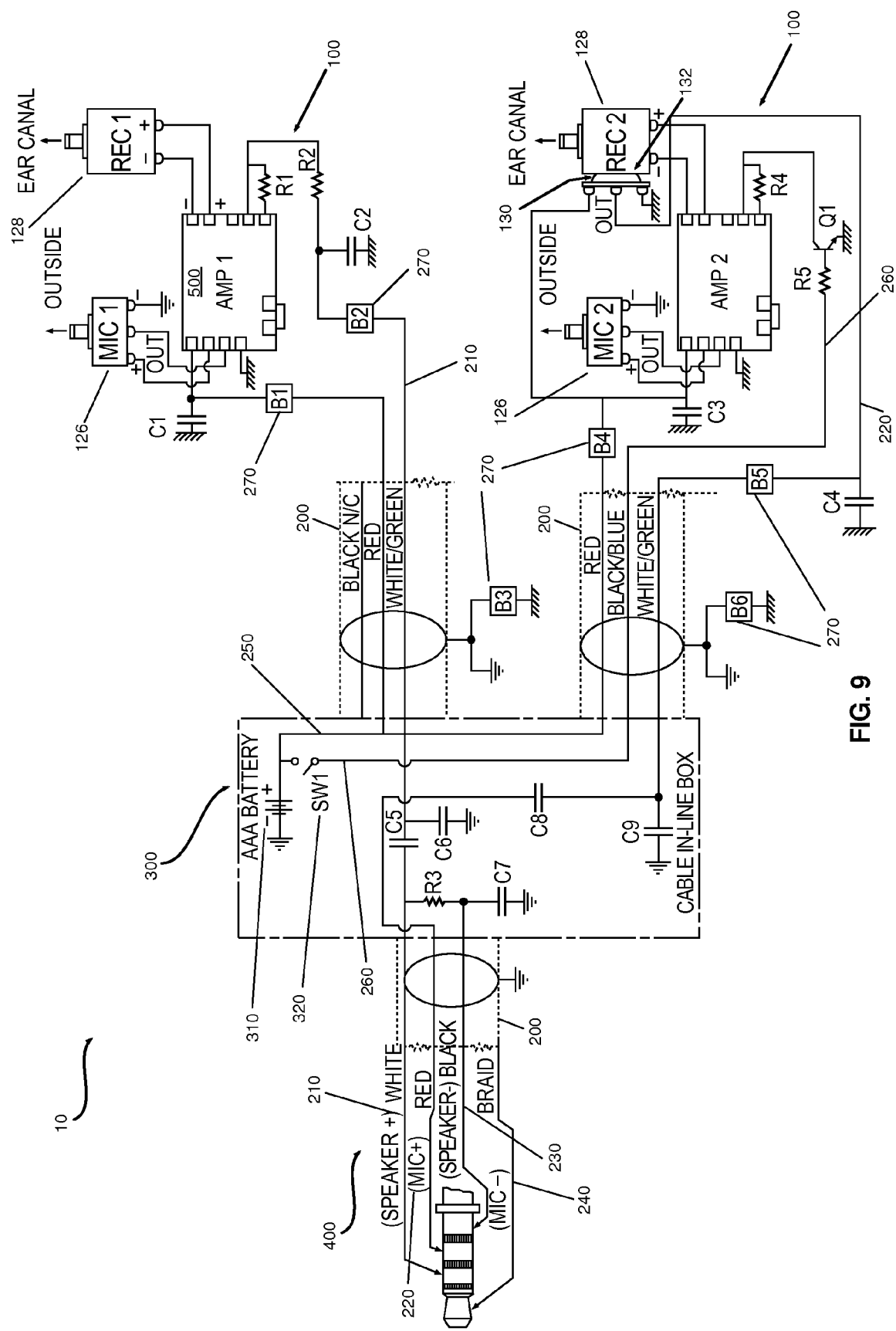
FIG. 9 depicts an exemplary circuit diagram of an exemplary communication and protection system comprising a plug, a battery module, cable, and electronic earplugs used in accordance with embodiments of the present technology.
Figure 11:
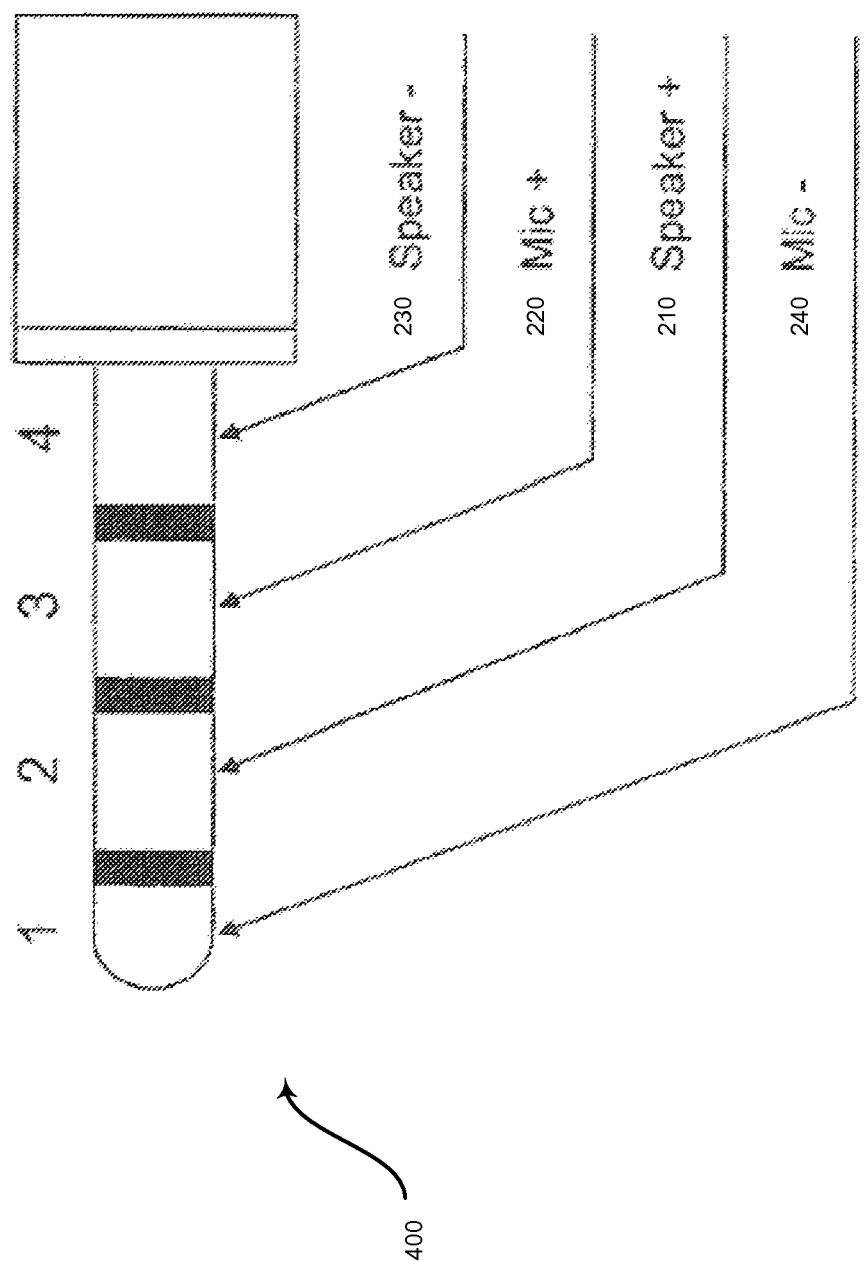
FIG. 11 depicts an exemplary wiring scheme for an exemplary plug used in accordance with embodiments of the present technology.
Figure 12:
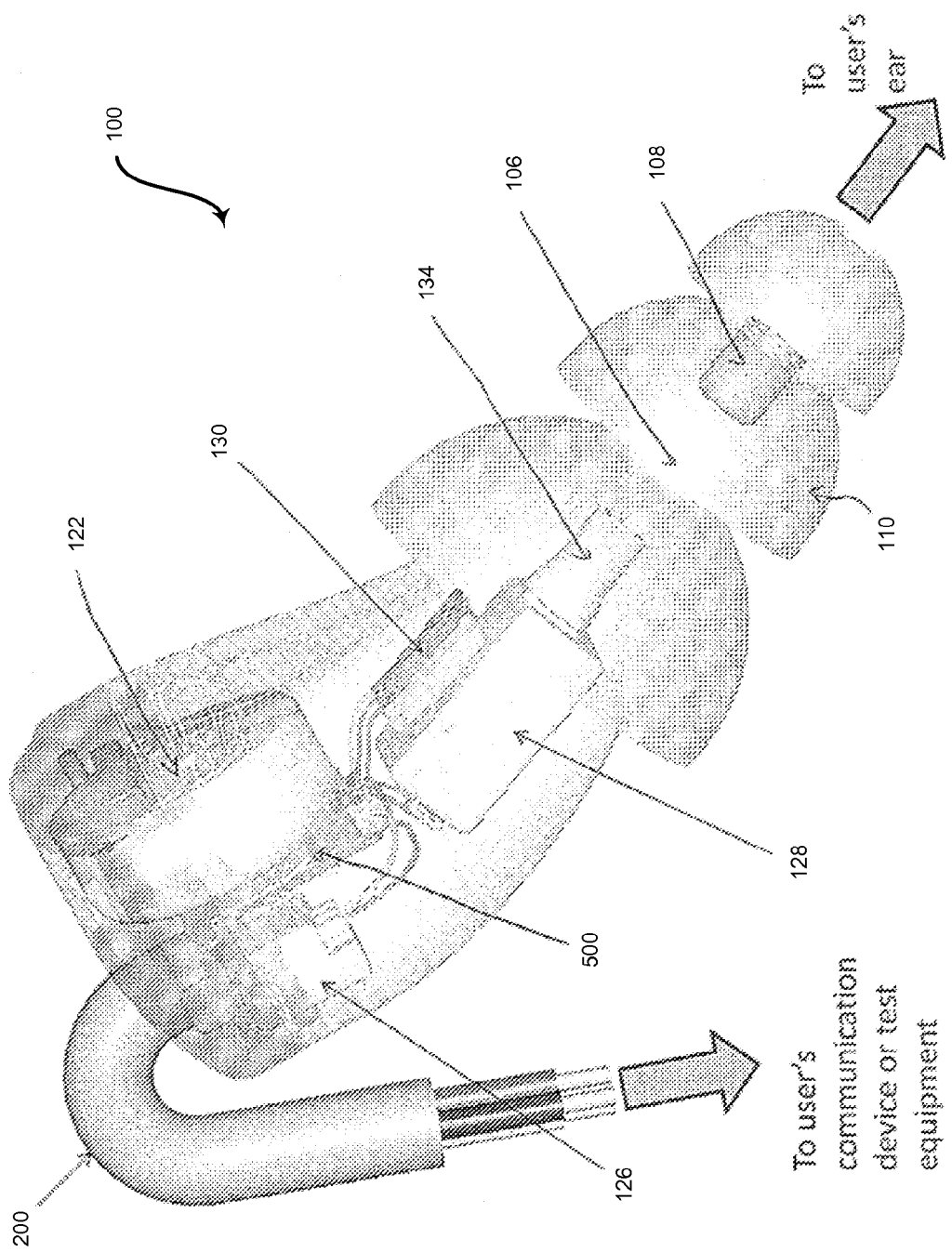
FIG. 12 depicts a perspective view of an exemplary electronic earplug used in accordance with embodiments of the present technology.

In certain embodiments, the battery module 300 may be a separate module as shown in FIGS. 1-3 and 9, for example. Additionally and/or alternatively, the battery module 300 can be incorporated in one or more of the electronic earplugs 100 as illustrated in FIGS. 6-7 and 12, for example. The battery module 300 may house a battery 310 operable to provide power to exterior microphone(s) 126, canal microphone(s) 130, receiver(s) 128, and/or processing circuitry 500 in the electronic earplugs 100, as illustrated in FIG. 9, for example. The battery 310 may be a AAA battery or any suitable battery, for example. Additionally and/or alternatively, one or more of the earplugs 100 may comprise a cell 122. The cell 122 may be a battery or a single cell, such as a 312 size zinc-air or lithium-ion cell, or any suitable cell. The cell 122 can be operable to provide power to exterior microphone(s) 126, canal microphone(s) 130, receiver(s) 128, and/or processing circuitry 500 in the electronic earplugs 100, as illustrated in FIGS. 6-7, 12, and 14, for example. The battery module 300 and/or the electronic earplugs 100 may couple to a jack of the push to talk assembly 600 using a cable 200 terminating at a plug 400, for example. The plug 400 may configured with a North Atlantic Treaty Organization (NATO) wiring scheme, as illustrated in FIGS. 9 and 11, or any suitable wiring scheme, for example.

The electronic earplugs 100 are configured to receive sound exterior to an ear canal at an exterior microphone 126. The exterior microphone 126 converts the sound to electrical signals and provide the electrical signals to a hybrid circuit 500, as discussed in more detail below. The hybrid circuit 500 can modify the sound level and pass electrical signals to a receiver 128. The receiver 128 converts the electrical signals to sound, which is communicated from the receiver 128 to a user's ear canal through a sound tube 106. The hybrid circuit 500 of electronic earplug 100 can be configured to attenuate sounds above a threshold sound pressure level.

One or more of the electronic earplugs 100 can be configured to receive sound, such as a user's voice, in an ear canal at an ear canal microphone 130. The ear canal microphone 130 converts the sound to electrical signals and provide the electrical signals to the communication radio 700 for transmission when the push to talk assembly 600 is in transmit mode.

The electronic earplugs 100 comprise a left ear earplug and a right ear earplug. The electronic earplugs 100 may couple to the push to talk assembly 600 using a cable 200 comprising a plug 400. The plug may be configured with a North Atlantic Treaty Organization (NATO) wiring scheme, as illustrated in FIGS. 9 and 11, or any suitable wiring scheme. The cable 200 may include one or more length adjusting sleeves 280 for shortening or lengthening the cable 200 and/or sections of cable 200.

Figure 2:
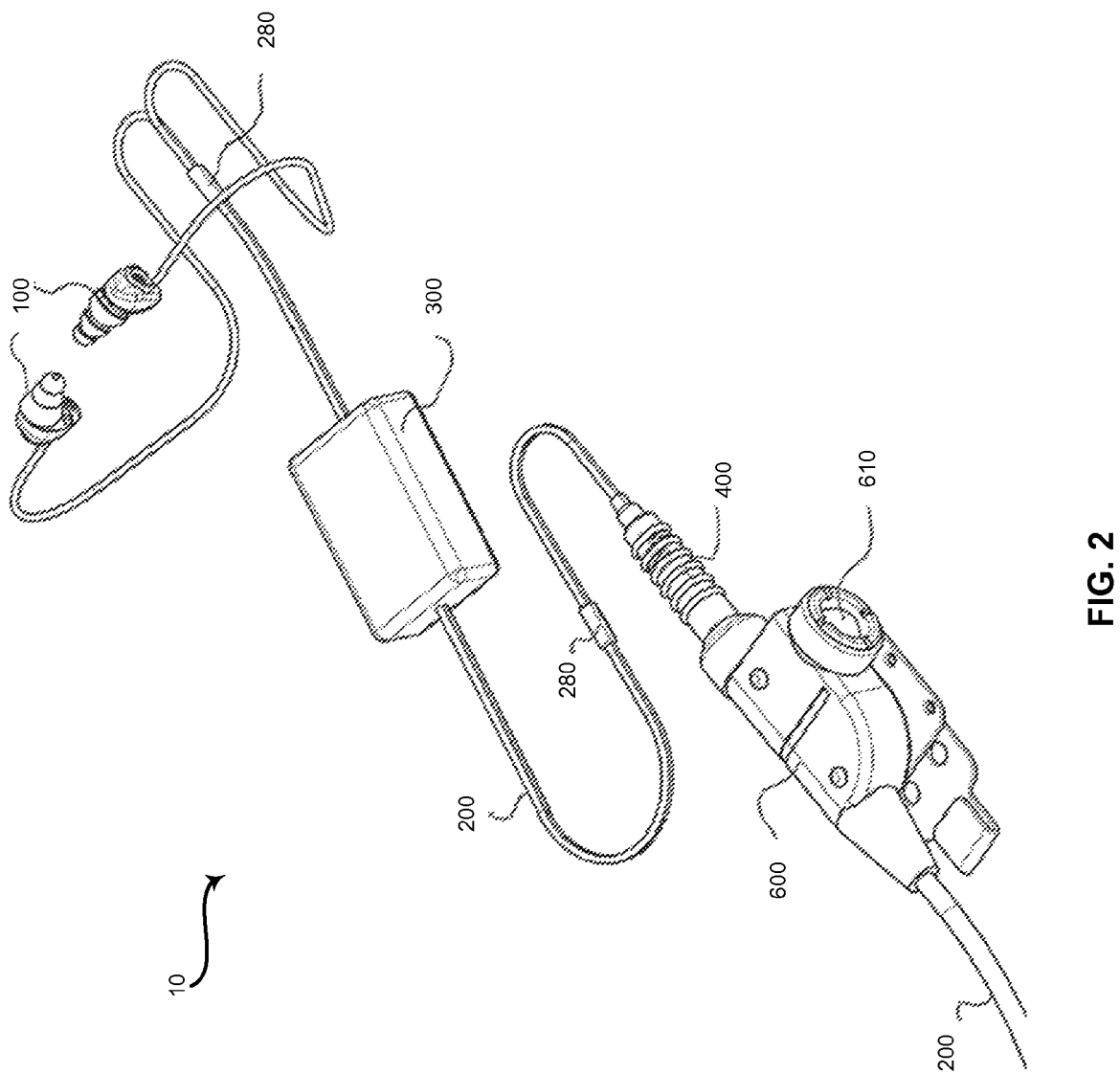
FIG. 2 depicts an exemplary communication and protection system comprising a push to talk assembly, a battery module, cables, and electronic earplugs used in accordance with embodiments of the present technology.
Figure 3:
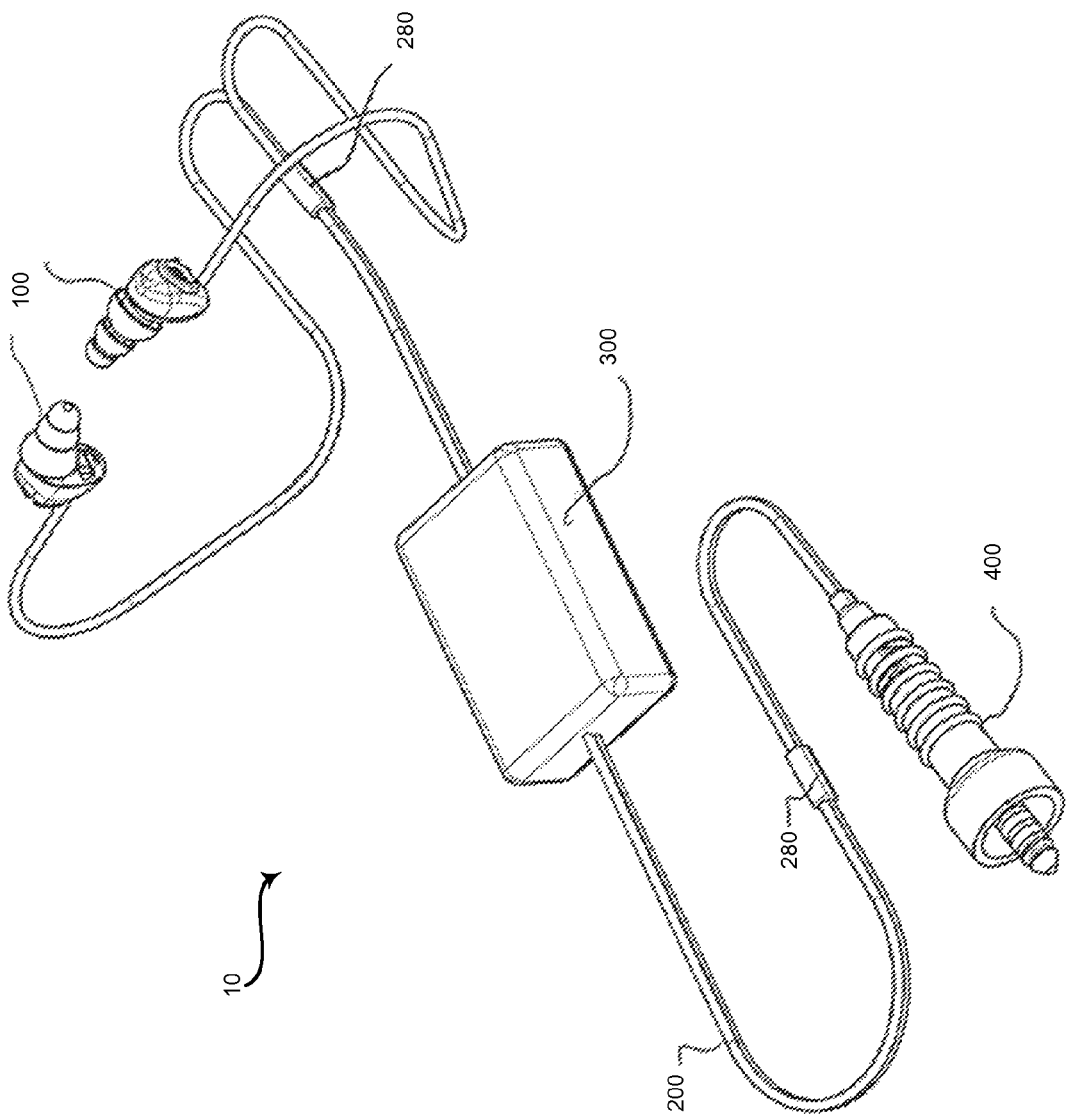
FIG. 3 depicts an exemplary communication and protection system comprising a battery module, cables, and electronic earplugs used in accordance with embodiments of the present technology.

FIG. 2 depicts an exemplary communication and protection system 10 comprising a push to talk assembly 600, a battery module 300, cable 200, and electronic earplugs 100 used in accordance with embodiments of the present technology. FIG. 3 depicts an exemplary communication and protection system 10 comprising a battery module 300, cable 200, and electronic earplugs 100 used in accordance with embodiments of the present technology. The communication and protection system 10 illustrated in FIGS. 2-3 shares various characteristics with the communication and protection system 10 illustrated in FIG. 1 as described above.

Figure 4:
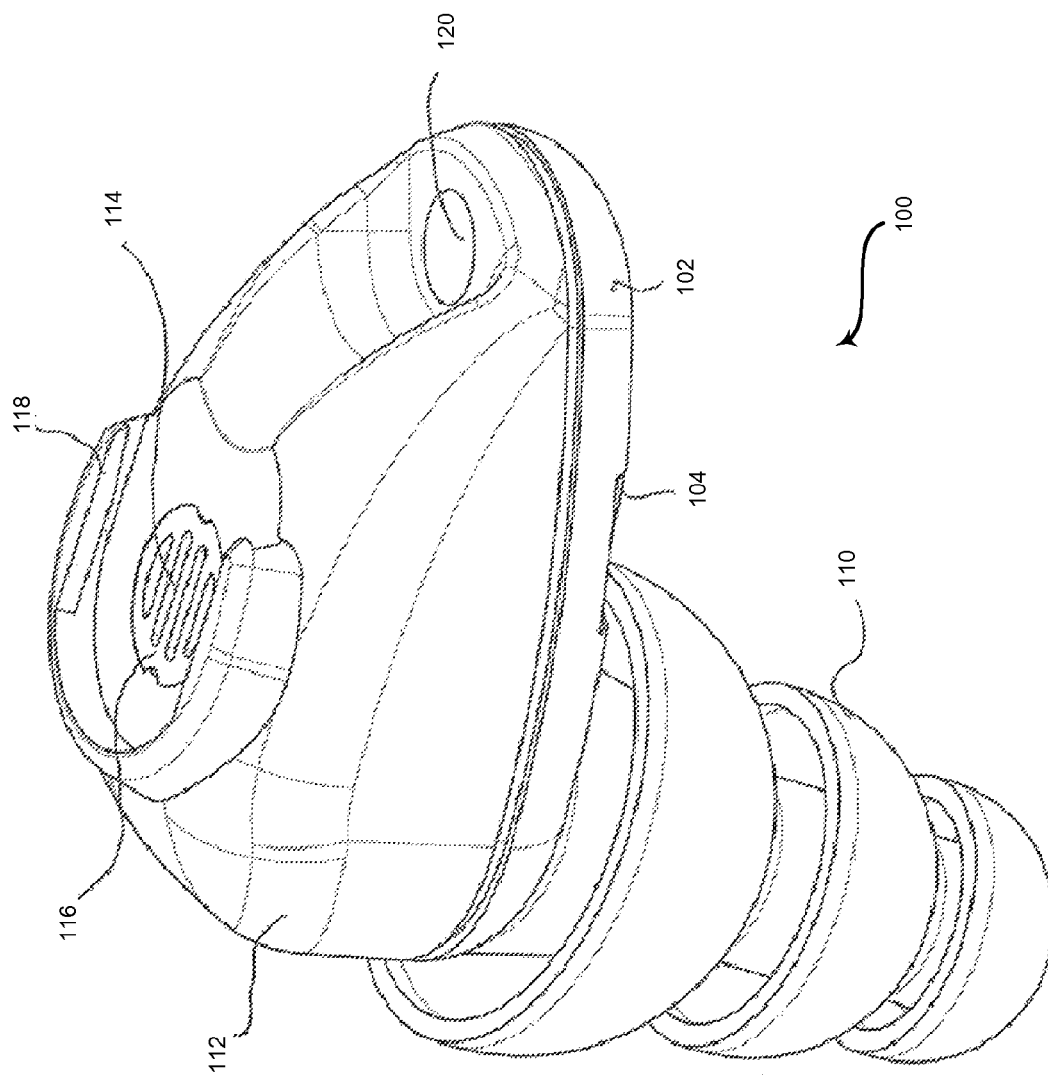
FIG. 4 depicts a side perspective view of an exemplary electronic earplug used in accordance with embodiments of the present technology.
Figure 5:
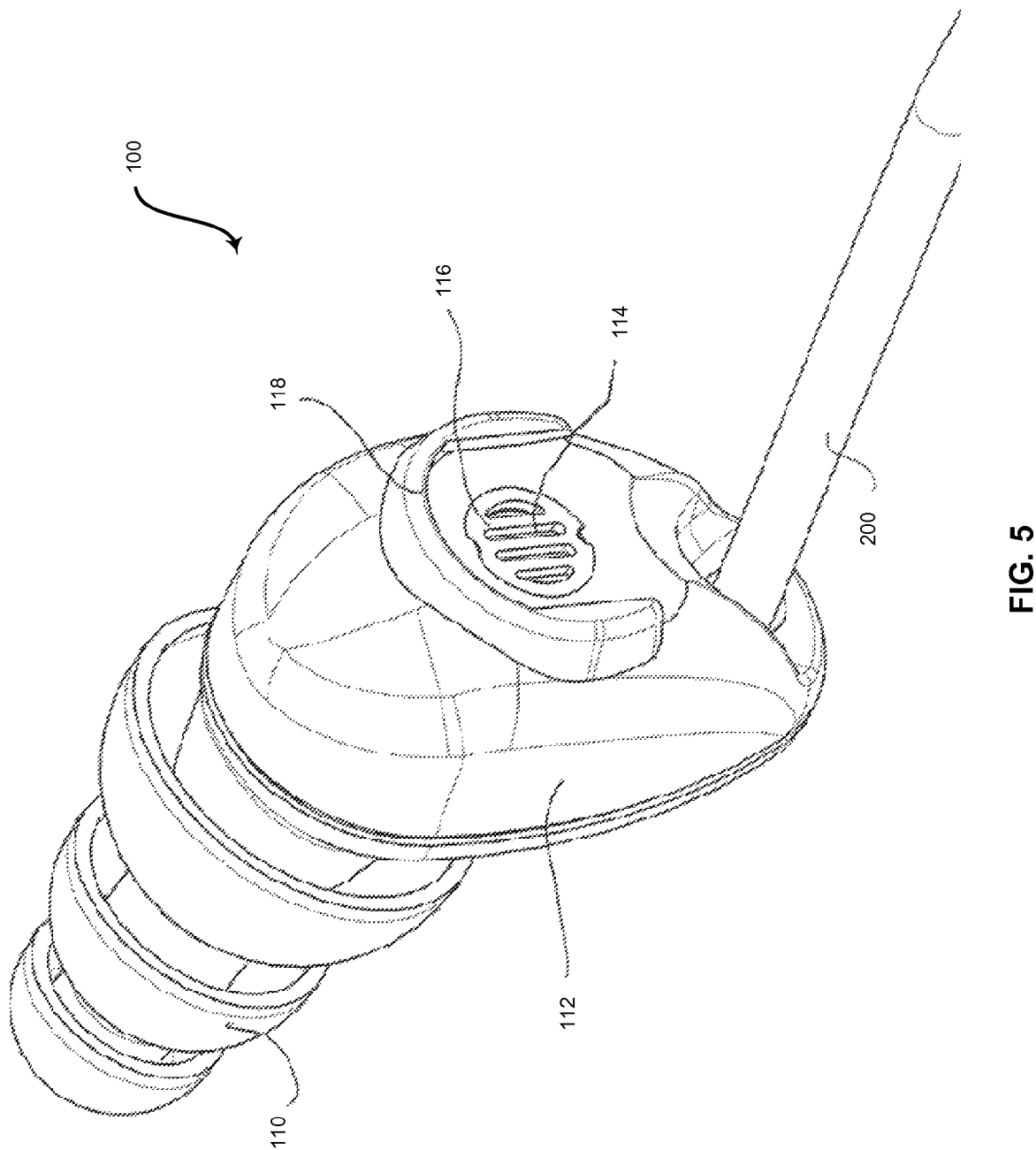
FIG. 5 depicts a rear perspective view of an exemplary electronic earplug used in accordance with embodiments of the present technology.

FIG. 4 depicts a side perspective view of an exemplary electronic earplug 100 used in accordance with embodiments of the present technology. FIG. 5 depicts a rear perspective view of an exemplary electronic earplug 100 used in accordance with embodiments of the present technology. Referring to FIGS. 4-5, the electronic earplug may comprise an eartip 110 and a housing 102, 112.

The eartip 110 may comprise three concentric circular flanges. The flanges can have increasing diameters, such that the flange furthest from the housing 102, 112 is the smallest, the flange closest to the housing 102, 112 is the largest, and the flange therebetween is an intermediate size. When inserted into a user's ear canal, the smallest flange enters first, and when fully inserted, the eartip can block exterior noise up to about 35 dB or more from entering the ear canal. Such eartips can come in other forms, such as a cylindrical foam eartip, a mushroom shaped foam eartip, or any suitable eartip.

The housing 102, 112 comprises a base 102 (as shown in FIG. 4) and a cover 112. The base 102 may comprise a cell door 104 for providing access to a cell 122. The cell 122 may be a battery or a single cell, such as a 312 size zinc-air or lithium-ion cell, or any suitable cell.

Referring again to FIGS. 4-5, the cover 112 can comprise an exterior microphone inlet 114 that may be adjacent to an acoustic damper (not shown) for smoothing a frequency response and an exterior microphone 126 that receives sound pressure levels exterior to the ear canal. The exterior microphone inlet 114 can include a dust screen 116 for preventing debris from entering the microphone inlet 114. In certain embodiments, the cover 112 can comprise a windscreen attachment mechanism 118 operable to receive a windscreen (not shown). The cover 112 of the housing 102, 112 may comprise an opening 120 for coupling with a cable 200.

Figure 8:
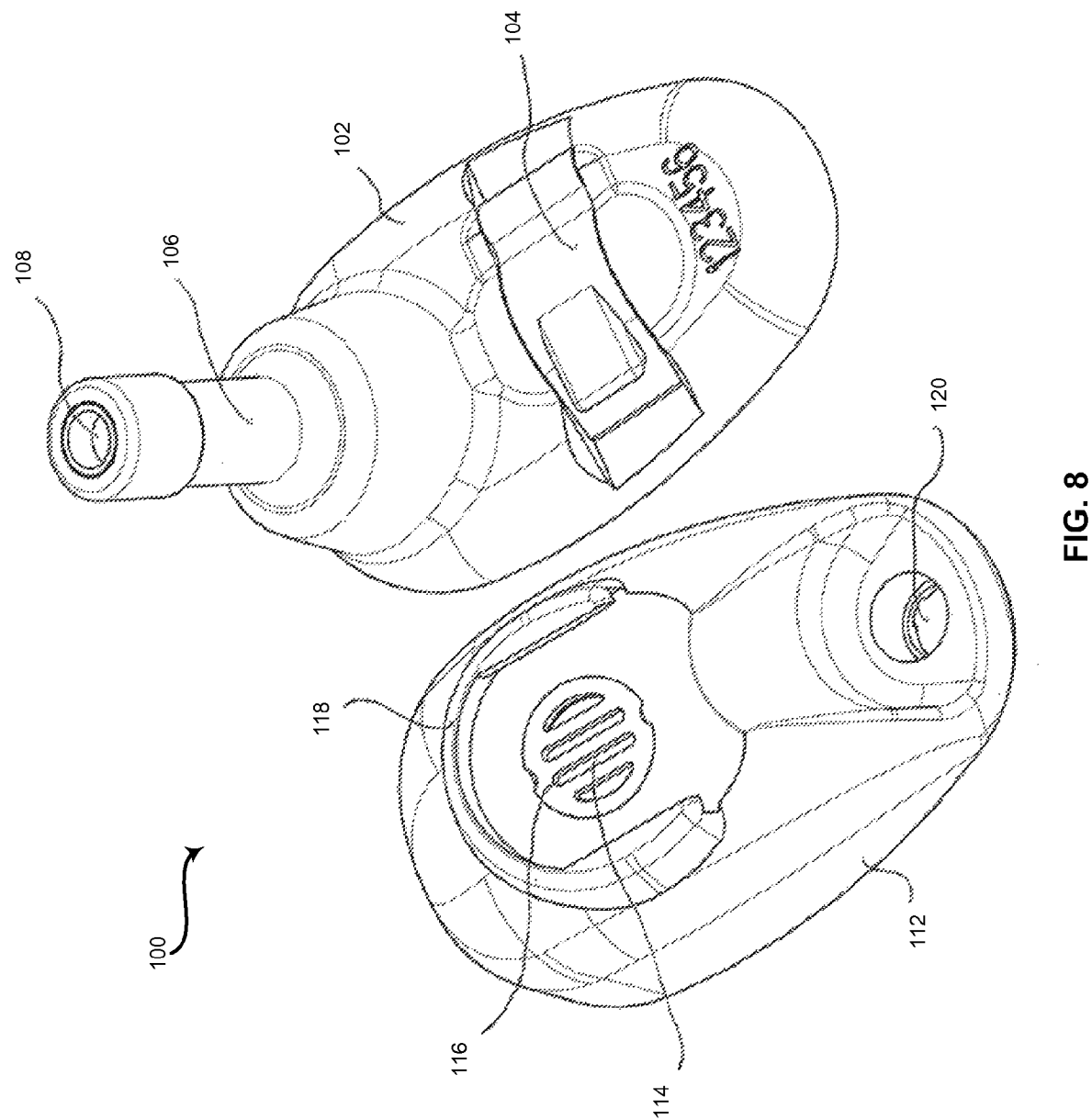
FIG. 8 depicts exemplary front and rear housing sections used in accordance with embodiments of the present technology.

FIG. 6 depicts an exemplary electronic earplug 100 with a canal microphone 130 used in accordance with embodiments of the present technology. FIG. 7 depicts an exemplary electronic earplug 100 without a canal microphone used in accordance with embodiments of the present technology. Referring to FIGS. 6-7, the electronic earplugs 100 comprise an eartip 110 and a housing 102, 112. The eartip attaches to a sound tube 106 (as shown in FIG. 8) comprising a flexible tube section 134.

The housing 102, 112 comprises a base 102 and a cover 112. An exterior microphone 126, a receiver 128, and processing circuitry 500 are disposed in the housing 102, 112. The exterior microphone 126 is configured to receive sound exterior to an ear canal. The exterior microphone 126 converts the received sound to electrical signals and provides the electrical signals to the processing circuitry 500, which may be a hybrid circuit shown in FIG. 10, or any suitable processing circuitry. The processing circuitry 500 can modify the sound level and pass electrical signals to the receiver 128. The receiver 128 converts the electrical signals to sound, which are communicated from the receiver to a user's ear canal through the sound tube 106 (as shown in FIG. 8). The electronic earplug 100 can be configured to attenuate sounds above a threshold sound pressure level.

Figure 13:
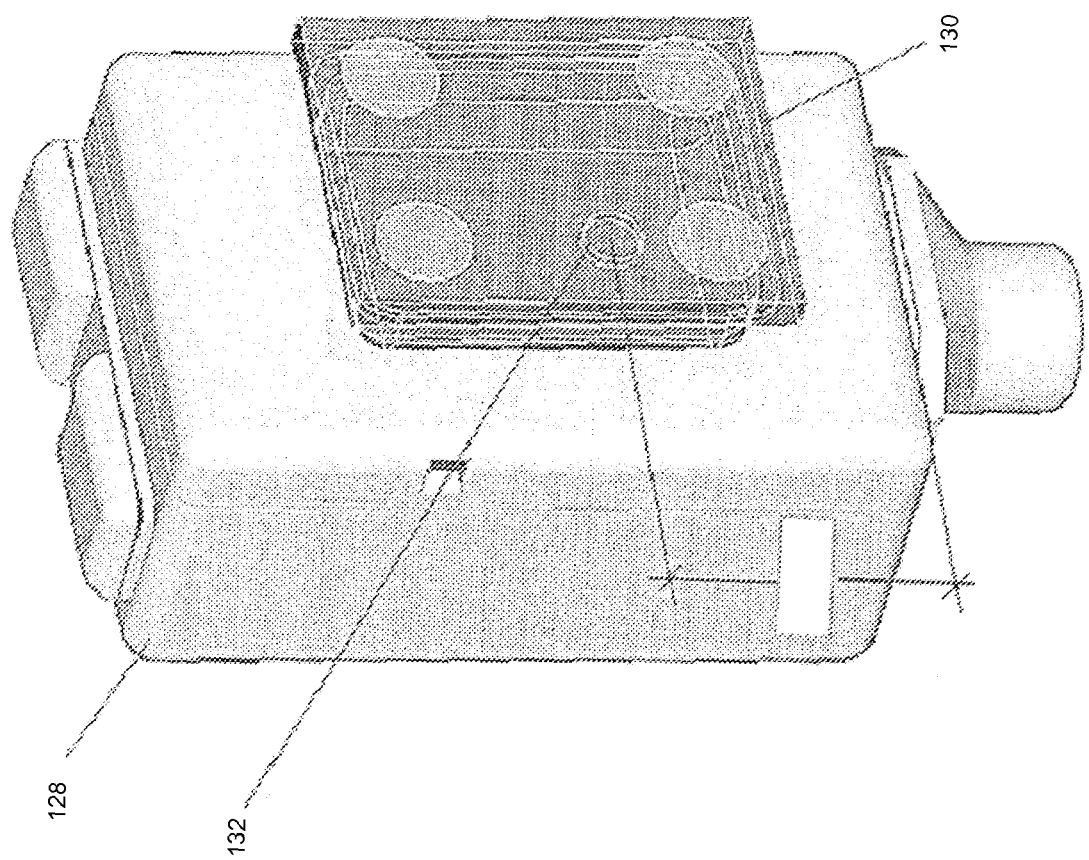
FIG. 13 depicts a perspective view of an exemplary receiver and canal microphone assembly used in accordance with embodiments of the present technology.

In certain embodiments, one or more of the electronic earplugs 100 may comprise an ear canal microphone 130 disposed in the housing 102, 112. The ear canal microphone 130 is coupled to the receiver 128 as shown in FIG. 13, for example, and configured to receive sound, such as a user's voice, in an ear canal through the sound tube 106. The ear canal microphone 130 converts the sound to electrical signals and provides the electrical signals to a communication radio 700 for transmission when a push to talk assembly 600 is in transmit mode, for example.

Certain embodiments provide that one of a pair of electronic earplugs 100 comprises the ear canal microphone 130. For example, a left ear earplug may include the ear canal microphone 130 and the right ear earplug may not include an ear canal microphone. In such embodiments, the receiver 128 of the right ear earplug may provide the processed sound from the exterior microphone 126 to the ear canal when the push to talk assembly 600 is in transmit mode, and may provide the processed sound from the exterior microphone 126 mixed with sound received from the communication radio 700 when the push to talk assembly 600 is in receive mode. Further, the receiver 128 of the left ear earplug may provide the processed sound from the exterior microphone 126 to the ear canal when the push to talk assembly 600 is in receive mode, and at least one of the receiver 128 and the exterior microphone 126 of the left ear earplug may be disabled when the push to talk assembly 600 is in transmit mode such that sound from an ear canal microphone 130 can be provided to the communication radio 700 for transmission.

Certain embodiments provide that both electronic earplugs 100 comprise the ear canal microphone 130. As one example, the ear canal microphone 130 in a first electronic earplug 100 may correspond with a first communication radio 700, and the ear canal microphone 130 in a second electronic earplug 100 can correspond with a second communication radio 700, among other things.

The electronic earplug 100 illustrated in FIGS. 6-7 shares various characteristics with the electronic earplugs 100 illustrated in FIGS. 1-5 as described above.

FIG. 8 depicts exemplary base 102 and cover 112 housing sections used in accordance with embodiments of the present technology. Referring to FIG. 8, the electronic earplug housing comprises a base 102 and a cover 112, for example. The cover 112 may include an exterior microphone inlet 114, a dust screen 116, a windscreen attachment 118, and/or a cable opening 120. The base 102 can include a cell door 104. A sound tube 106, operable to carry sound from a receiver 128 to an ear canal and/or from an ear canal to a canal microphone 130, may extend from the base 102. The sound tube 106 may comprise a damper 108 configured to smooth a frequency response. The electronic earplug housing 102, 112 illustrated in FIG. 8 shares various characteristics with the electronic earplug 100 illustrated in FIGS. 1-7 as described above.

Figure 10:
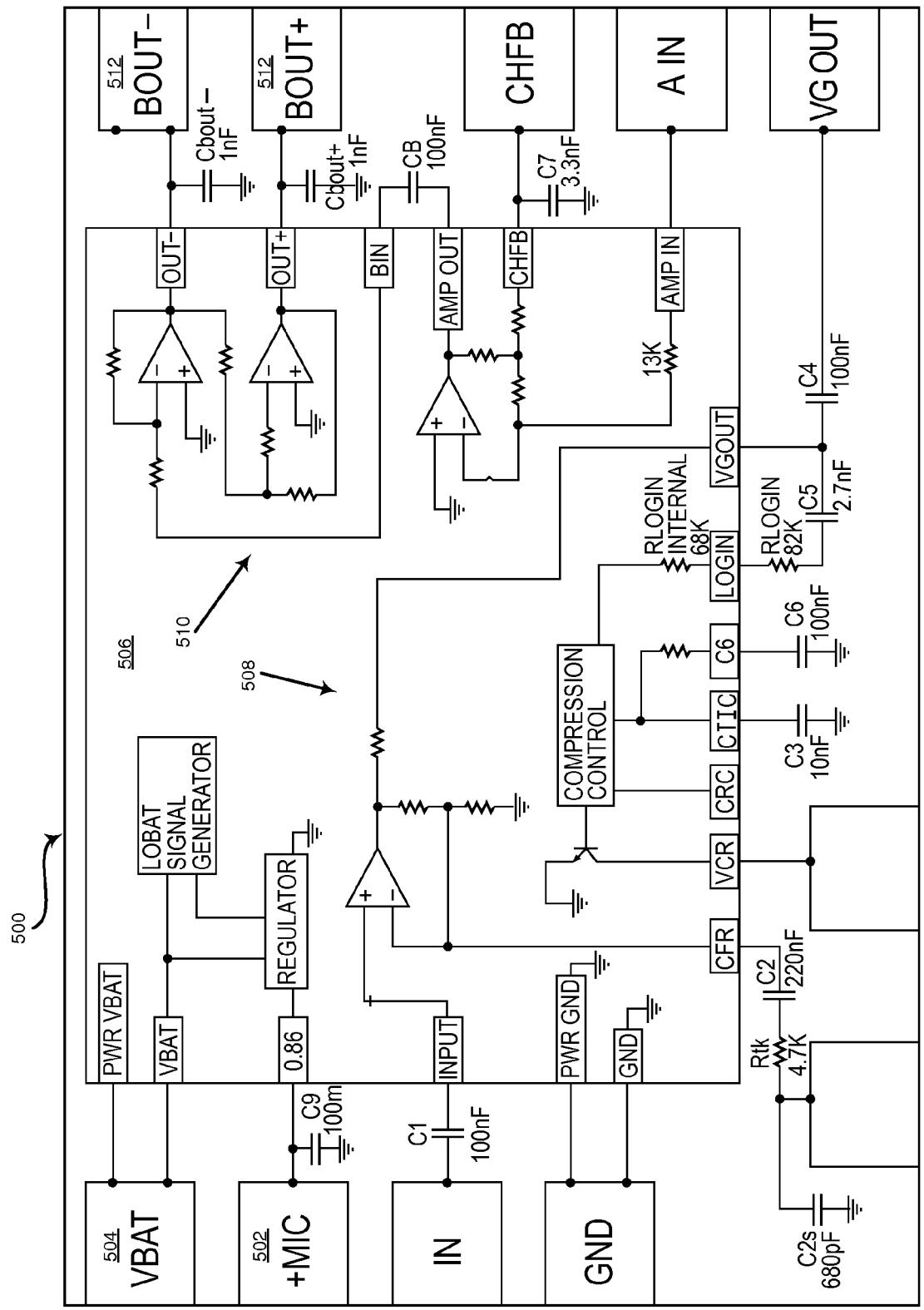
FIG. 10 depicts an exemplary circuit diagram of exemplary processing circuitry for electronic earplugs used in accordance with embodiments of the present technology.

FIG. 9 depicts an exemplary circuit diagram of an exemplary communication and protection system 10 comprising a plug 400, a battery module 300, cable 200, and electronic earplugs 100 used in accordance with embodiments of the present technology. FIG. 10 depicts an exemplary circuit diagram of exemplary processing circuitry 500 for electronic earplugs 100 used in accordance with embodiments of the present technology. FIG. 11 depicts an exemplary wiring scheme for an exemplary plug 400 used in accordance with embodiments of the present technology.

Referring to FIG. 9, the electronic earplug circuitry comprises plug circuitry 400, battery module circuitry 300, electrical signal lines 210-260 of a cable 200, right ear earplug circuitry 100, and left ear earplug circuitry 100, for example. Although the earplug circuitry 100 may be designated as right ear earplug circuitry and left ear earplug circuitry, the right ear earplug circuitry may alternatively be designated for the left ear, and the left ear earplug circuitry may be designated for the right ear.

The plug circuitry 400 is operable to mate with a jack at a communication radio 700. The plug circuitry 400 can be a North Atlantic Treaty Organization (NATO) plug connector having a wiring scheme as shown in FIG. 11, or any suitable wiring scheme. The plug circuitry can include a speaker+ 210, a mic+ 220, a speaker− 230, and a mic− 240. The speaker+ 210 may provide electrical signals from a communication radio 700 to the right ear earplug 100, for example, when a push to talk assembly switch 610 and/or battery module switch 320 is switched to a receive mode. The mic+ 220 can provide electrical signals from an ear canal microphone 130 in the left ear earplug 100, for example, when a push to talk assembly switch 610 and/or a battery module switch 320 is switched to a transmit mode. For example, switching the battery module switch 320 to a transmit position can disable one or more of the external microphone 126, the receiver 128, and the processing circuitry 500 of the left ear earplug 100 via electrical signal line 260. The speaker− 230 and mic− 240 electrical signal lines are grounded.

The battery module circuitry (e.g., cable in-line box) 300 comprises a battery 310, such as a AAA battery or any suitable battery. The battery module circuitry 300 provides power via electrical signal line 250 to right ear earplug circuitry 100 and the left ear earplug circuitry 100. For example, the battery module circuitry 300 may provide power to the exterior microphones (e.g., MIC1 and MIC2) 126, canal microphone (e.g., MEMS MIC) 130, receivers (e.g., REC1 and REC2) 128, and/or processing circuitry (e.g., AMP1 and AMP2) 500 in the electronic earplugs 100. The battery module circuitry 300 can include a switch (e.g., SW1) 320 operable to disable one or more of the exterior microphone (e.g., MIC2) 126, the receiver (e.g., REC2) 128, and the processing circuitry (e.g., AMP2) 500 of the left ear earplug 100 via electrical signal line 260 when the system 10 is in transmit mode. Additionally and/or alternatively, a switch 610 of a push to talk assembly 600 may be operable to disable at least one of the exterior microphone (e.g., MIC2) 126, the receiver (e.g., REC2) 128, and the processing circuitry (e.g., AMP2) 500 of the left ear earplug 100 when the system 10 is in transmit mode.

The right ear earplug circuitry 100 comprises an exterior microphone (e.g., MIC1) 126, a receiver (e.g., REC1) 128, and processing circuitry (e.g., AMP1) 500. The exterior microphone 126 receives sound exterior to an ear canal, for example. The exterior microphone 126 converts the received sound to electrical signals and provides the electrical signals to the processing circuitry 500. The processing circuitry 500 can modify the sound level and pass electrical signals to the receiver 128. The processing circuitry 500 may be an ER-43F hybrid amplifier as shown in FIG. 10, or any suitable processing circuitry. The receiver 128 converts the electrical signals to sound, which is communicated from the receiver 128 to a user's ear canal through a sound tube 106. The processing circuitry 500 of the electronic earplug 100 can be configured to attenuate sounds above a threshold sound pressure level.

The processing circuitry 500 of the right ear earplug 100 can also receive electrical signals from a communication radio 700, for example, when a push to talk assembly 600 is switched to a receive mode. The electrical signals from the communication radio 700 provided via electrical signal line 210 can be mixed with the electrical signals from exterior microphone (e.g., MIC1) 126 at processing circuitry 500, and the mixed electrical signals are converted to sound and provided to a user's ear canal by the receiver 128.

The left ear earplug circuitry 100 comprises an exterior microphone (e.g., MIC2) 126, a receiver (e.g., REC2) 128, an ear canal microphone (e.g., MEMS MIC) 130 and processing circuitry (e.g., AMP2) 500. The exterior microphone 126 receives sound exterior to an ear canal. The exterior microphone 126 converts the received sound to electrical signals and provides the electrical signals to the processing circuitry 500. The processing circuitry 500 can modify the sound level and pass electrical signals to the receiver 128. The processing circuitry 500 may be an ER-43F hybrid amplifier as shown in FIG. 10, or any suitable processing circuitry. The receiver 128 converts the electrical signals to sound, which is communicated from the receiver 128 to a user's ear canal through a sound tube 106. The processing circuitry 500 of the electronic earplug 100 can be configured to attenuate sounds above a threshold sound pressure level.

The ear canal microphone 130 of the left ear earplug 100 is configured to receive sound, such as a user's voice, in an ear canal. The ear canal microphone 130 can be a Micro Electrical-Mechanical System (MEMS) microphone or any suitable microphone. The ear canal microphone 130 converts the sound to electrical signals and provides the electrical signals to the communication radio 700 via electrical signal line 220 for transmission when the push to talk assembly switch 610 and/or the battery module switch 320 is in transmit mode.

One or more of the electrical signal lines 210-260 of cable 200 may comprise low pass filters (e.g., boxes B1 to B6) 270 configured to block radio frequency signals generated by the communication radio 700 from interfering with the right ear earplug circuitry 100 and the left ear earplug circuitry 100. The low pass filters 270 may be, for example, no-pass LC notch filters constructed by winding 3.3 turns of wire around a 100 pF capacitor and/or a low pass chip inductor.

Referring to FIG. 10, the electronic earplug processing circuitry 500 comprises a microphone 502 terminal corresponding with exterior microphone 126, a battery terminal 504 corresponding with battery 320, and an amplification circuit 506. The microphone terminal 502 is shown connected to the regulated supply, but it will be readily understood that such microphones 126 have an output terminal that is connected to the IN terminal of the circuit 508, and a ground terminal that is connected to the GND terminal of circuit 508. The amplification circuit 506 includes circuitry 508 and circuitry 510. Circuitry 508 can include the elements shown, which elements are described in further detail in U.S. Pat. No. 5,131,046, entitled "High Fidelity Hearing Aid Amplifier," which issued to Killion et al. and is incorporated herein by reference in its entirety. Such circuitry is that which is used in K-AMP® hearing aids described previously. Circuitry 510 can include the circuit 601 described in connection with FIG. 3 of U.S. Pat. No. 8,160,284, entitled "Amplification Circuit and Hearing Aid," which issued to Johnson et al. and is incorporated herein by reference in its entirety. Further, circuitry 508 and circuitry 510 can be implemented as an integrated circuit.

Referring again to FIG. 10, the battery terminal 504 can receive power for the electronic earplug processing circuitry 500. The microphone terminal 502 can receive ambient sound and convert the sound into electrical signals. The electrical signals can be communicated to the amplification circuit 506. The amplification circuit 506 can be configured to process received signals and communicate the processed signals to a two-terminal receiver 128 via outputs 512. The receiver 128 can convert the processed signals into sound and communicate the sound to a user of the electronic earplug 100. In certain embodiments, the electronic earplug processing circuitry 500 can provide frequency response accuracy of at least about 80 percent.

FIG. 12 depicts a perspective view of an exemplary electronic earplug 100 used in accordance with embodiments of the present technology. Referring to FIG. 12, the electronic earplug 100 comprises a canal microphone 130, an exterior microphone 126, processing circuitry 500, a cell 122, a sound tube 106, an eartip 110, and a cable 200. The sound tube 106 may comprise a flexible tube 134 and a damper 108. The electronic earplug 100 illustrated in FIG. 12 shares various characteristics with the electronic earplug(s) 100 illustrated in FIGS. 1-7 and 9 as described above.

FIG. 13 depicts a perspective view of an exemplary receiver 128 and canal microphone 130 assembly used in accordance with embodiments of the present technology. Referring to FIG. 13, a canal microphone 130 comprising a hole 132 is shown coupled to a receiver 128 comprising a hole 132. The receiver 128 and the canal microphone 130 are coupled such that the hole 132 in the receiver 128 is aligned with the hole 132 in the canal microphone 130. In operation, when in transmit mode, the receiver 128 can be disabled and the canal microphone 130 receives sound, such as a user's voice, from an ear canal. The sound travels from the ear canal, through a sound tube 106 into the receiver 128, and through the hole 132 in the receiver 128 into the canal microphone 130. When in receive mode, the receiver 128 is enabled and receives electrical signals from processing circuitry 500. The receiver 128 converts the received electrical signals to sound, which is communicated from the receiver 128 to a user's ear canal through a sound tube 106.

Figure 14:
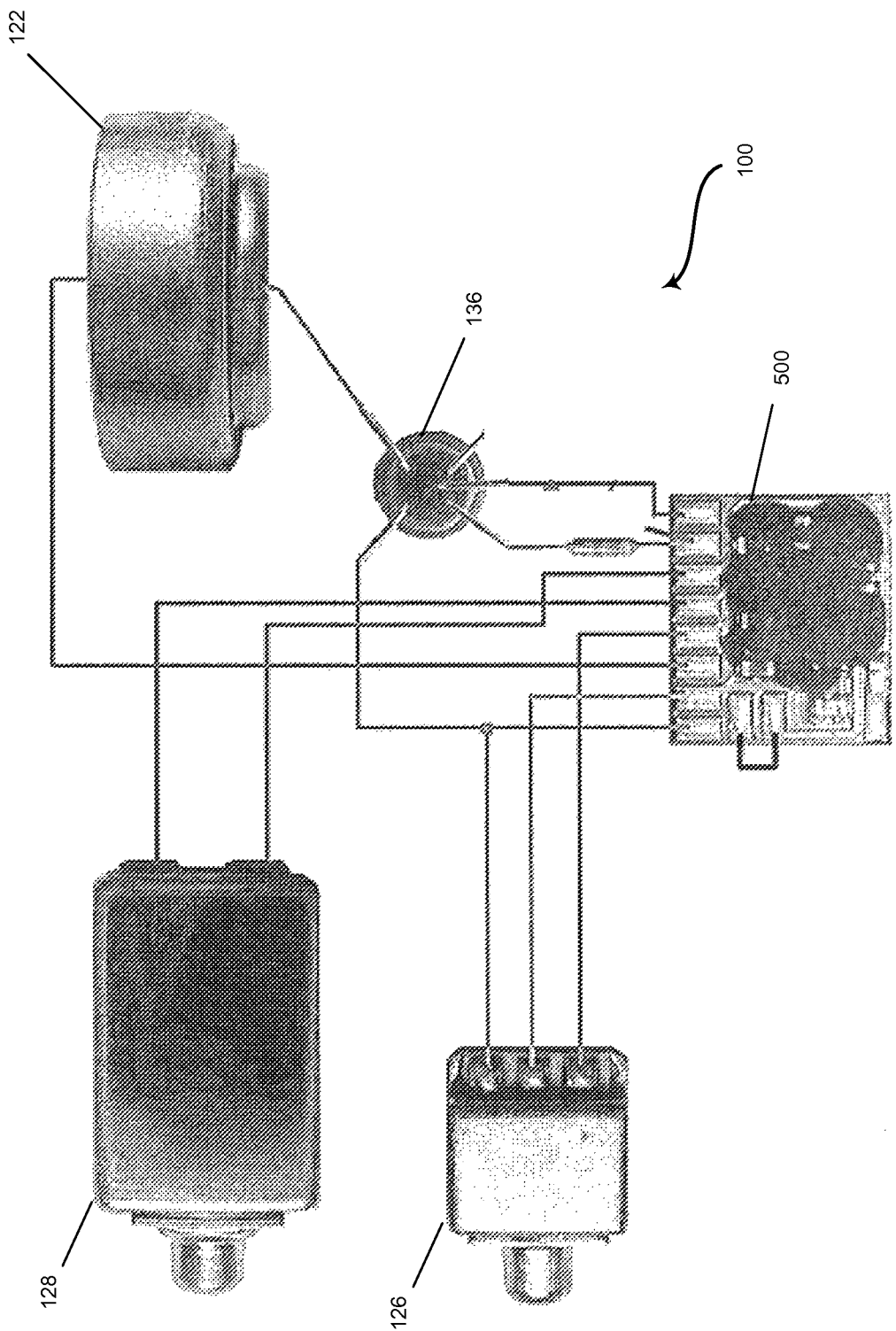
FIG. 14 depicts an exemplary circuit diagram of an exemplary electronic earplug used in accordance with embodiments of the present technology.

FIG. 14 depicts an exemplary circuit diagram of an exemplary electronic earplug 100 used in accordance with embodiments of the present technology. Referring to FIG. 14, the electronic earplug circuitry 100 comprises an exterior microphone 126, a receiver 128, a battery 122, processing circuitry 500, and a volume control 136, for example. The volume control 136 sets an amplification level of the processing circuitry 500 to adjust the volume of the sound provided to a user's ear canal by the receiver 128. The electronic earplug 100 illustrated in FIG. 14 shares various characteristics with the electronic earplug 100 and associated components illustrated in FIGS. 1-10 and 12-13 as described above.

Figure 15:
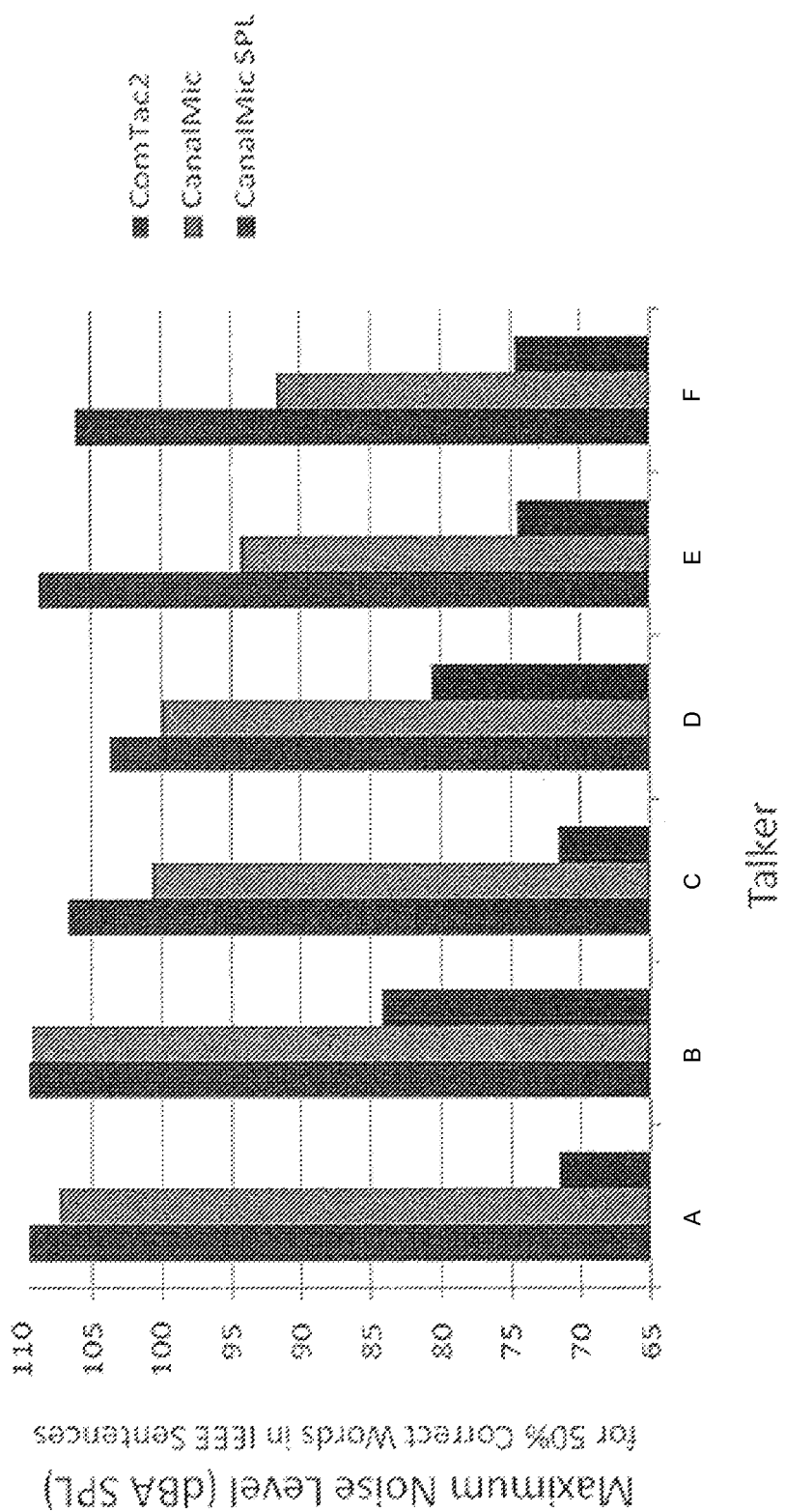
FIG. 15 is a graph depicting maximum noise level for six talkers using a canal microphone in accordance with embodiments of the present technology compared with the maximum noise level for six talkers using a ComTac II boom microphone.

FIG. 15 is a graph depicting maximum noise level for six talkers using a canal microphone in accordance with embodiments of the present technology compared with the maximum noise level for six talkers using a ComTac II boom microphone.

Figure 16:
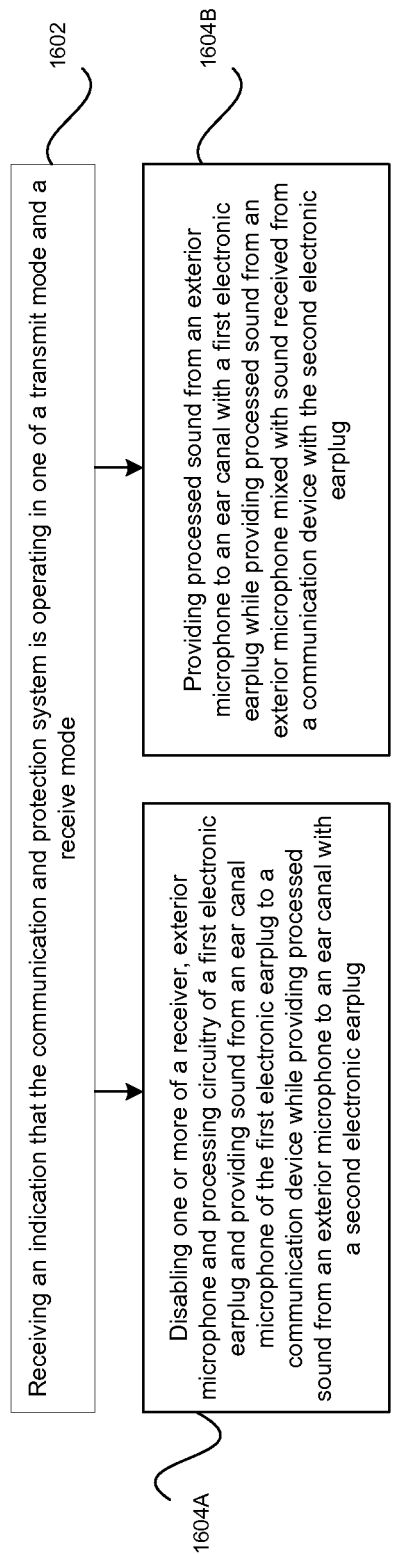
FIG. 16 is a flow chart illustrating exemplary steps that may be utilized for providing communication and protection by an electronic earplug, in accordance with an embodiment of the invention.

FIG. 16 is a flow chart illustrating exemplary steps that may be utilized for providing communication and protection by an electronic earplug 100, in accordance with an embodiment of the invention. Referring to FIG. 16, there is shown a flow chart 1600 comprising exemplary steps 1602 through 1604A-B.

In step 1602, one or more of the electronic earplugs 100 receive an indication that the communication and protection system 10 is operating in one of a transmit mode and a receive mode. For example, a push to talk assembly 600 coupling a communication radio 700 with the electronic earplugs 100 can provide the mode indication. The push to talk assembly 600 comprises a switch 610, such as a momentary switch or any suitable switching mechanism, for switching between a transmit mode and a reception mode. For example, when a switch 610 of the push to talk assembly 600 is actuated, the communication system 10 is operable to transmit communications, and when the switch 610 is not actuated, the system 10 is operable to receive communications, or vice versa. Additionally and/or alternatively, a battery module 300 coupling a communication radio 700 with the electronic earplugs 100 can provide the mode indication. The battery module 300 may comprise a switch 320, such as a momentary switch or any suitable switching mechanism, for switching between a transmit mode and a reception mode. For example, when a switch 320 of the battery module 300 is actuated, the communication system 10 is operable to transmit communications, and when the switch 320 is not actuated, the system 10 is operable to receive communications, or vice versa. The mode indication can be provided, for example, via electrical signal line 210 and/or electrical signal line 260 as illustrated in FIG. 9.

In steps 1604A-B, the electronic earplugs are operable to operate in one of the transmit mode and the receive mode based on the indication received at step 1602. For example, if the mode indication received at step 1602 is for the transmit mode, the method can proceed to step 1604A. In step 1604A, one or more of a receiver 128, an exterior microphone 126, and processing circuitry 500 of a first electronic earplug 100 are disabled via electrical signal line 260 such that sound from an ear canal microphone 130 of the first electronic earplug 100 can be provided via electrical signal line 220 to the communication radio 700 for transmission while a second electronic earplug 100 provides processed sound from an exterior microphone 126 to an ear canal.

As another example, if the mode indication received at step 1602 is for the receive mode, the method can proceed to step 1604B. In step 1604B, a first electronic earplug 100 provides processed sound from an exterior microphone 126 to the ear canal while a second electronic earplug 100 provides processed sound from an exterior microphone 126 mixed with sound received from a communication radio 700 via electrical signal line 210.

Aspects of the present invention provide communication and protection by electronic earplugs 100. In accordance with various embodiments of the invention, a communication and protection system 10 comprises a first electronic earplug 100 operable in a transmit mode and a receive mode. The first electronic earplug 100 comprises a first external microphone 126 configured to transduce sound pressure levels received from exterior to an ear canal to electrical signals when operating in the receive mode. The first electronic earplug 100 comprises an ear canal microphone 130 configured to transduce sound pressure levels received from in the ear canal to electrical signals provided to a communication device 700 when operating in the transmit mode. The first electronic earplug 100 comprises first processing circuitry 500 configured to process the electrical signals from the first external microphone 126 to provide first processed electrical signals when operating in the receive mode. The first electronic earplug 100 comprises a first receiver 128 configured to convert the first processed electrical signals to sound when operating in the receive mode. One or more of the first external microphone 126, the first processing circuitry 500, and the first receiver 128 is disabled when operating in the transmit mode.

In a representative embodiment, the communication and protection system 10 comprises a second electronic earplug 100 operable in the transmit mode and the receive mode. The second electronic earplug 100 comprises a second external microphone 126 configured to transduce sound pressure levels received from exterior to an ear canal to electrical signals. The second electronic earplug 100 comprises second processing circuitry 500 configured to process the electrical signals from the second external microphone 126 to provide second processed electrical signals when operating in the transmit mode. The second processing circuitry 500 is configured to process the electrical signals from the second external microphone 126 mixed with electrical signals received from the communication device 700 to provide the second processed electrical signals when operating in the receive mode. The second electronic earplug 100 comprises a second receiver 128 configured to convert the second processed electrical signals to sound.

The communication and protection system 10 comprises a switch 320, 610 configured to provide one of a plurality of mode indications to at least one of the first electronic earplug 100 and the second electronic earplug 100. The plurality of mode indications comprises a transmit mode indication corresponding with operation in the transmit mode and a receive mode indication corresponding with operation in the receive mode. In certain embodiments, the communication and protection system 10 comprises a push to talk assembly 600 coupling at least one of the first electronic earplug 100 and the second electronic earplug 100 with the communication device 700. The push to talk assembly 600 comprises the switch 610. In a representative embodiment, the communication and protection system 10 comprises a battery module 300 coupling at least one of the first electronic earplug 100 and the second electronic earplug 100 with the communication device 700. The battery module 300 comprises a battery 310 operable to provide power to at least one of the first electronic earplug 100 and the second electronic earplug 100. In various embodiments, the battery module 300 comprises the switch 310.

The communication device 700 may be a communication radio. In a representative embodiment, the communication and protection system 10 comprises a cell 122 configured to provide power to the first external microphone 126, the ear canal microphone 130, the first processing circuitry 500, and the first receiver 128. The cell 122 may be a 312 size zinc-air or lithium-ion cell. In various embodiments, the ear canal microphone 130 is a Micro Electrical-Mechanical System (MEMS) microphone. The first electronic earplug 100 is coupled with the communication device 700 by at least one cable 200. The at least one cable 200 may comprise at least one length adjusting sleeve 280. In various embodiments, the at least one cable 200 comprises a plug 400 configured with a North Atlantic Treaty Organization (NATO) wiring scheme.

In a representative embodiment, the first processing circuitry 500 is configured to process the electrical signals from the first external microphone 126 to provide the first processed electrical signals by at least attenuating sounds above a threshold sound pressure level. Each of the ear canal microphone 130 and the first receiver 128 may comprise a hole 132. The ear canal microphone 130 is coupled to the first receiver 128 such that the holes 132 are aligned. The ear canal microphone 130 receives the sound pressure levels from in the ear canal through the holes 132. The communication and protection system 10 can comprise a volume control 136 operable to set an amplification level of the first processed electrical signals processed by the first processing circuitry 500.

The communication and protection system 10 comprises a housing 102, 112. The first external microphone 126, the ear canal microphone 130, the first processing circuitry 500, and the first receiver 128 are disposed in the housing 102, 112. The housing 102, 112 comprises a base 102 and a cover 112. The cover 112 comprises an exterior microphone inlet 114. In a representative embodiment, the exterior microphone inlet 114 comprises a dust screen 116. The base 102 may comprise a cell door 104.

The communication and protection system 10 comprises a sound tube 106 operable to carry the sound from the first receiver 128 to the ear canal and to carry the sound pressure levels received from in the ear canal to the ear canal microphone 130. The sound tube 106 extends from the base 102. In a representative embodiment, the sound tube 106 is coupled to the first receiver 128 at a flexible tube 134. The sound tube 106 can comprise a damper 108 disposed within the sound tube 106.

Various embodiments provide a method 1600 for providing communication and protection. The method 1600 comprises receiving 1610, at a first electronic earplug 100, a mode indication that the first electronic earplug 100 is operating in one of a transmit mode and a receive mode.

If the received mode indication is that the first electronic earplug 100 is operating in a receive mode 1604B, the method 1600 comprises transducing, at a first external microphone 126, sound pressure levels received from exterior to an ear canal to electrical signals. The method 1600 comprises processing, at first processing circuitry 500, the electrical signals from the first external microphone 126 to provide first processed electrical signals. The method 1600 comprises converting, at a first receiver 128, the first processed electrical signals to sound.

If the received mode indication is that the first electronic earplug 100 is operating in a transmit mode 1604A, the method 1600 comprises transducing, at an ear canal microphone 130, sound pressure levels received from in the ear canal to electrical signals provided to a communication device 700. The method 1600 comprises disabling at least one of the first external microphone 126, the first processing circuitry 500, and the first receiver 128.

If the received mode indication is that the first electronic earplug 100 is operating in a receive mode 1604B, the method 1600 comprises transducing, at a second external microphone 100, sound pressure levels received from exterior to an ear canal to electrical signals. The method 1600 comprises processing, at second processing circuitry 500, the electrical signals from the second external microphone 126 mixed with electrical signals received from the communication device 700 to provide second processed electrical signals. The method 1600 comprises converting, at a second receiver 128, the second processed electrical signals to sound.

If the received mode indication is that the first electronic earplug 100 is operating in a transmit mode 1604A, the method 1600 comprises transducing, at the second external microphone 126, sound pressure levels received from exterior to the ear canal to electrical signals. The method 1600 comprises processing, at the second processing circuitry 500, the electrical signals from the second external microphone 126 to provide the second processed electrical signals. The method 1600 comprises converting, at the second receiver 128, the second processed electrical signals to sound.

The received mode indication is provided by a switch 610, 320 of at least one of a push to talk assembly 600 and a battery module 300. The method 1600 comprises providing power to at least one of the first electronic earplug 100 and the second electronic 100 by one or more of a battery module 300 comprising a battery 310, and a cell 122 disposed within a housing 102, 112 of at least one of the first electronic earplug 100 and the second electronic earplug 100.

The processing the electrical signals from the first external microphone 126 to provide the first processed electrical signals is performed by at least attenuating sounds above a threshold sound pressure level. The method 1600 may comprise receiving, by the ear canal microphone 130, sound pressure levels from in the ear canal through aligned holes 132 in each of the ear canal microphone 130 and the first receiver 128. The method 1600 can comprise setting, by a volume control 136, an amplification level of the first processed electrical signals processed by the first processing circuitry 500. The method 1600 comprises carrying, by a sound tube 106 coupled to the first receiver 128 and extending from a housing 102, 112 of the first electronic earplug 100, the sound from the first receiver 128 to the ear canal and the sound pressure levels received from in the ear canal to the ear canal microphone 130.

As utilized herein the term "circuitry" refers to physical electronic components (i.e. hardware) and any software and/or firmware ("code") which may configure the hardware, be executed by the hardware, and or otherwise be associated with the hardware. As used herein, for example, a particular processor and memory may comprise a first "circuit" when executing a first one or more lines of code and may comprise a second "circuit" when executing a second one or more lines of code. As utilized herein, circuitry is "operable" to perform a function whenever the circuitry comprises the necessary hardware and code (if any is necessary) to perform the function, regardless of whether performance of the function is disabled, or not enabled, by some user-configurable setting.

Although devices, methods, and systems according to the present invention may have been described in connection with a preferred embodiment, it is not intended to be limited to the specific form set forth herein, but on the contrary, it is intended to cover such alternative, modifications, and equivalents, as can be reasonably included within the scope of the invention as defined by this disclosure and appended diagrams.

While the present invention has been described with reference to certain embodiments, it will be understood by those skilled in the art that various changes may be made and equivalents may be substituted without departing from the scope of the present invention. In addition, many modifications may be made to adapt a particular situation or material to the teachings of the present invention without departing from its scope. Therefore, it is intended that the present invention not be limited to the particular embodiment disclosed, but that the present invention will include all embodiments falling within the scope of the appended claims.

What is claimed is:

1. A communication and protection system comprising:
a first electronic earplug operable in a transmit mode and a receive mode, the first electronic earplug comprising:
a first external microphone configured to transduce sound pressure levels received from exterior to an ear canal to electrical signals when operating in the receive mode,
an ear canal microphone configured to transduce sound pressure levels received from in the ear canal to electrical signals provided to a communication device when operating in the transmit mode,
first processing circuitry configured to process the electrical signals from the first external microphone to provide first processed electrical signals when operating in the receive mode, and
a first receiver configured to convert the first processed electrical signals to sound when operating in the receive mode,
wherein at least one of the first external microphone, the first processing circuitry, and the first receiver is disabled when operating in the transmit mode.

2. The system according to claim 1, comprising a second electronic earplug operable in the transmit mode and the receive mode, the second electronic earplug comprising:
a second external microphone configured to transduce sound pressure levels received from exterior to an ear canal to electrical signals,
second processing circuitry configured to:
process the electrical signals from the second external microphone to provide second processed electrical signals when operating in the transmit mode, and
process the electrical signals from the second external microphone mixed with electrical signals received from the communication device to provide the second processed electrical signals when operating in the receive mode, and
a second receiver configured to convert the second processed electrical signals to sound.

3. The system according to claim 2, comprising a switch configured to provide one of a plurality of mode indications to at least one of the first electronic earplug and the second electronic earplug, the plurality of mode indications comprising a transmit mode indication corresponding with operation in the transmit mode and a receive mode indication corresponding with operation in the receive mode.

4. The system according to claim 3, comprising a push to talk assembly coupling at least one of the first electronic earplug and the second electronic earplug with the communication device, the push to talk assembly comprising the switch.

5. The system according to claim 3, comprising a battery module coupling at least one of the first electronic earplug and the second electronic earplug with the communication device, the battery module comprising:
a battery operable to provide power to at least one of the first electronic earplug and the second electronic earplug, and
the switch.

6. The system according to claim 2, wherein the communication device is a communication radio.

7. The system according to claim 1, comprising a cell configured to provide power to the first external microphone, the ear canal microphone, the first processing circuitry, and the first receiver.

8. The system according to claim 7, wherein the cell is a 312 size zinc-air or lithium-ion cell.

9. The system according to claim 1, wherein the ear canal microphone is a Micro Electrical-Mechanical System (MEMS) microphone.

10. The system according to claim 1, wherein the first electronic earplug is coupled with the communication device by at least one cable.

11. The system according to claim 10, wherein the at least one cable comprises at least one length adjusting sleeve.

12. The system according to claim 10, wherein the at least one cable comprises a plug configured with a North Atlantic Treaty Organization (NATO) wiring scheme.

13. The system according to claim 1, wherein the first processing circuitry is configured to process the electrical signals from the first external microphone to provide the first processed electrical signals by at least attenuating sounds above a threshold sound pressure level.

14. The system according to claim 1, wherein each of the ear canal microphone and the first receiver comprises a hole, and the ear canal microphone is coupled to the first receiver such that the holes are aligned.

15. The system according to claim 14, wherein the ear canal microphone receives the sound pressure levels from in the ear canal through the holes.

16. The system according to claim 1, comprising a volume control operable to set an amplification level of the first processed electrical signals processed by the first processing circuitry.

17. The system according to claim 1, comprising a housing, wherein the first external microphone, the ear canal microphone, the first processing circuitry, and the first receiver are disposed in the housing, and wherein the housing comprises a base and a cover.

18. The system according to claim 17, wherein cover comprises an exterior microphone inlet.

19. The system according to claim 18, wherein the exterior microphone inlet comprises a dust screen.

20. The system according to claim 17, wherein the base comprises a cell door.

21. The system according to claim 17, comprising a sound tube operable to carry the sound from the first receiver to the ear canal and to carry the sound pressure levels received from in the ear canal to the ear canal microphone, the sound tube extending from the base.

22. The system according to claim 21, wherein the sound tube is coupled to the first receiver at a flexible tube.

23. The system according to claim 21, wherein the sound tube comprises a damper disposed within the sound tube.

24. A method for providing communication and protection comprising:
receiving, at a first electronic earplug, a mode indication that the first electronic earplug is operating in one of a transmit mode and a receive mode; and
if the received mode indication is that the first electronic earplug is operating in a receive mode:
transducing, at a first external microphone, sound pressure levels received from exterior to an ear canal to electrical signals,
processing, at first processing circuitry, the electrical signals from the first external microphone to provide first processed electrical signals, and
converting, at a first receiver, the first processed electrical signals to sound, and
if the received mode indication is that the first electronic earplug is operating in a transmit mode:
transducing, at an ear canal microphone, sound pressure levels received from in the ear canal to electrical signals provided to a communication device, and
disabling at least one of the first external microphone, the first processing circuitry, and the first receiver.

25. The method according to claim 24, comprising:
if the received mode indication is that the first electronic earplug is operating in a receive mode:
transducing, at a second external microphone, sound pressure levels received from exterior to an ear canal to electrical signals,
processing, at second processing circuitry, the electrical signals from the second external microphone mixed with electrical signals received from the communication device to provide second processed electrical signals, and
converting, at a second receiver, the second processed electrical signals to sound, and
if the received mode indication is that the first electronic earplug is operating in a transmit mode:
transducing, at the second external microphone, sound pressure levels received from exterior to the ear canal to electrical signals,
processing, at the second processing circuitry, the electrical signals from the second external microphone to provide the second processed electrical signals, and
converting, at the second receiver, the second processed electrical signals to sound.

26. The method according to claim 25, wherein the received mode indication is provided by a switch of at least one of a push to talk assembly and a battery module.

27. The method according to claim 25, comprising providing power to at least one of the first electronic earplug and the second electronic by at least one of:
a battery module comprising a battery, and
a cell disposed within a housing of at least one of the first electronic earplug and the second electronic earplug.

28. The method according to claim 24, wherein the processing the electrical signals from the first external microphone to provide the first processed electrical signals is performed by at least attenuating sounds above a threshold sound pressure level.

29. The method according to claim 24, comprising receiving, by the ear canal microphone, sound pressure levels from in the ear canal through aligned holes in each of the ear canal microphone and the first receiver.

30. The method according to claim 24, comprising setting, by a volume control, an amplification level of the first processed electrical signals processed by the first processing circuitry.

31. The method according to claim 24, comprising carrying, by a sound tube coupled to the first receiver and extending from a housing of the first electronic earplug, the sound from the first receiver to the ear canal and the sound pressure levels received from in the ear canal to the ear canal microphone.

* * * * *